United States Patent [19]
Ferrini

[11] Patent Number: 5,286,728
[45] Date of Patent: Feb. 15, 1994

[54] AMINO-SUBSTITUTED PIPERAZINE DERIVATIVES

[75] Inventor: Pier G. Ferrini, Binningen, Switzerland

[73] Assignee: Ciba-Geigy Corporation, Ardsley, N.Y.

[21] Appl. No.: 913,277

[22] Filed: Jul. 14, 1992

[30] Foreign Application Priority Data

Jul. 19, 1991 [CH] Switzerland .......... 2160/91
Apr. 27, 1992 [CH] Switzerland .......... 1340/92

[51] Int. Cl.$^5$ ............... A61K 31/495; C07D 295/185; C07D 295/192; C07D 401/12
[52] U.S. Cl. .................. 514/255; 514/227.8; 514/235.8; 514/252; 544/60; 544/121; 544/357; 544/360; 544/372; 544/391; 562/432
[58] Field of Search ............. 544/391, 60, 121, 357, 544/360, 372; 514/255, 227.8, 235.8, 252

[56] References Cited

U.S. PATENT DOCUMENTS

| | | | |
|---|---|---|---|
| 3,926,961 | 12/1975 | Ferrini et al. | 544/391 |
| 4,505,913 | 3/1985 | Ferrini et al. | 544/391 |
| 4,804,661 | 2/1989 | Ferrini et al. | 514/255 |

FOREIGN PATENT DOCUMENTS

| | | |
|---|---|---|
| 250361 | 12/1987 | European Pat. Off. |
| 385043 | 9/1990 | European Pat. Off. |
| 489690 | 6/1992 | European Pat. Off. |
| 2365988 | 3/1977 | Fed. Rep. of Germany |
| 874096 | 8/1961 | United Kingdom |
| 2220206 | 1/1990 | United Kingdom |
| 9000548 | 1/1990 | World Int. Prop. O. |

OTHER PUBLICATIONS

Ferrini et al., Chemical Abstracts, vol. 117, No. 131227, (Abstract for EP489690, Jun. 10, 1992), (1992).
Metz et al., J. Med. Chem., 26, (1983), 1065–1070, Cloxacepride and Related Compounds: A New Series of Orally Active Antiallergic Compounds.
Lis et al., J. Med. Chem., 33, (1990), 2883–2891, Synthesis of Novel (Aryloxy) Propanolamines and Related Compounds Possessing Both Class II and Class III Antiarrythmic Activity.
Agarwal et al., Chem. Abstr., 100:174780c (1984).
Botros et al., Chem. Abstr., 112:235261f (1990).
Jacob et al., Chem. Abstr., 56:10165c (1962).
Jacob et al., Chem. Abstr., 57:15126h (1962).
Jacob et al., Chem. Abstr., 58:3444e (1963).
Rhone-Poulenc, Chem. Abstr., 58:4583f (1963).
Jacob et al., Chem. Abstr., 58:10211g (1963).

Primary Examiner—Emily Bernhardt
Attorney, Agent, or Firm—Irving M. Fishman; Karen G. Kaiser; Barbara J. Ikeler

[57] ABSTRACT

Amino-substituted piperazine derivatives of formula I

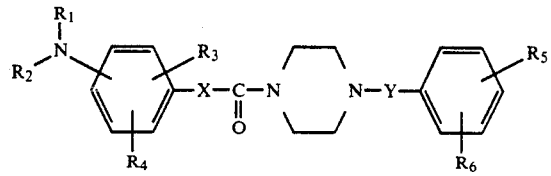

wherein $R_1$–$R_6$, X and Y are as defined in the description, and salts thereof, have properties inhibiting the biosynthesis of interleukin-1 (IL-1) as well as analgesic properties and can therefore be used as active ingredients in medicaments. They are prepared in a manner known per se.

16 Claims, No Drawings

AMINO-SUBSTITUTED PIPERAZINE DERIVATIVES

The invention relates to novel amino-substituted piperazine derivatives of formula I

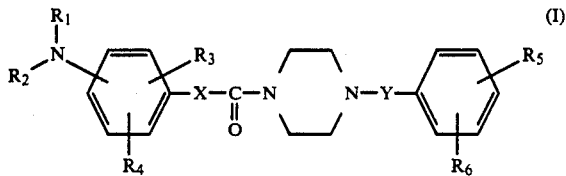

wherein $R_1$ is hydrogen, lower alkyl, lower alkoxy-lower alkyl, lower alkoxy-lower alkoxy-lower alkyl, aryloxy-lower alkyl, aryl-lower alkoxy-lower alkyl, N-lower alkylamino-lower alkyl or N,N-di-lower alkylamino-lower alkyl, $R_2$ is lower alkenoyl, (carboxy or lower alkoxycarbonyl)-lower alkenoyl, electronegatively substituted lower alkanoyl, carbamoyl, N-lower alkylcarbamoyl, N,N-di-lower alkylcarbamoyl, carboxycarbonyl, lower alkoxycarbonylcarbonyl, (carbamoyl, N-lower alkylcarbamoyl or N,N-di-lower alkylcarbamoyl)-carbonyl, or, when $R_1$ is lower alkoxy-lower alkyl, lower alkoxy-lower alkoxy-lower alkyl, aryloxy-lower alkyl, aryl-lower alkoxy-lower alkyl, N-lower alkylamino-lower alkyl or N,N-di-lower alkylamino-lower alkyl, $R_2$ may also be hydrogen, lower alkanoyl, carboxy, lower alkoxycarbonyl or aryl-lower alkoxycarbonyl, $R_3$ and $R_4$ are each independently of the other hydrogen, lower alkyl, halogen, lower alkoxy or lower alkylthio, $R_5$ and $R_6$ are each independently of the other hydrogen, lower alkyl, halo-lower alkyl, lower alkoxy, lower alkylthio, halogen, amino, lower alkylamino, di-lower alkylamino or lower alkanoylamino, and X and Y are each independently of the other a direct bond, lower alkylene or lower alkenylene, and to salts thereof, to processes for the preparation of those compounds, to pharmaceutical compositions comprising those compounds, and to the use of those compounds for the therapeutic treatment of the human or animal body or for the preparation of pharmaceutical compositions.

Electronegatively substituted lower alkanoyl is, for example, lower alkanoyl substituted by halogen, amino, lower alkylamino, (carboxy or lower alkoxycarbonyl)-lower alkylamino, di-lower alkylamino; 4- to 6-membered lower alkyleneamino, for example piperidino; morpholino, thiomorpholino, piperazino-which is unsubstituted or substituted in the 4-position by lower alkyl or by lower alkanoyl-, hydroxy, lower alkoxy, acyloxy, lower alkylthio, lower alkylsulfinyl, lower alkylsulfonyl, arylthio, arylsulfinyl, arylsulfonyl, carboxy, lower alkoxycarbonyl, carbamoyl, N-lower alkylcarbamoyl, N,N-di-lower alkylcarbamoyl or by cyano.

Hereinbefore and hereinafter, lower radicals and compounds are to be understood as being, for example, radicals and compounds having up to and including 7, preferably up to and including 4, carbon atoms (C atoms).

Lower alkyl is, for example, $C_1-C_7$alkyl, preferably $C_1-C_4$alkyl, such as, especially, methyl or, secondly, ethyl, n-propyl, isopropyl or n-butyl, but it may also be, for example, isobutyl, sec-butyl, tert-butyl or a pentyl, hexyl or heptyl group.

Halo-lower alkyl is, for example, trifluoromethyl.

Lower alkenoyl is, for example, $C_3-C_7$alkenoyl, preferably $C_3-C_5$alkenoyl, such as prop-2-enoyl (acryloyl), 2-methylprop-2-enoyl (methacryloyl), but-2-enoyl, but-3-enoyl, 3-methylbut-3-enoyl or pent-4-enoyl.

Halogen is especially chlorine or fluorine or also bromine, but it may also be iodine.

Halo-lower alkanoyl is, for example, halo-$C_2-C_7$alkanoyl, halogen being especially chlorine or, secondly, fluorine or bromine, preferably chloro-$C_2-C_4$alkanoyl, such as chloroacetyl, 3-chloropropionyl or 4-chlorobutyryl.

Di-lower alkylamino-lower alkanoyl is, for example, di-$C_1-C_4$alkylamino-$C_2-C_7$alkanoyl, and is preferably N,N-dimethylamino-$C_2-C_4$alkanoyl, such as dimethylaminoacetyl.

4- to 6-membered lower alkyleneamino-lower alkanoyl is, for example, pyrrolidino-$C_2-C_4$alkanoyl and preferably piperidino-$C_2-C_4$alkanoyl, for example piperidinoacetyl.

Lower alkoxy-lower alkyl carries the lower alkoxy group preferably in a position higher than the α-position and is, for example, corresponding $C_1-C_4$alkoxy-$C_2-C_4$alkyl, such as 2-methoxyethyl, 2-ethoxyethyl, 2-propoxyethyl, 2-isopropoxyethyl, 3-methoxypropyl, 3-ethoxypropyl, 3-isopropoxypropyl or 4-methoxybutyl.

Carboxycarbonyl is the group —C(=O)—COOH.

Aryl is, for example, phenyl that is unsubstituted or substituted by one or two substituents from the group consisting of lower alkyl, lowr alkoxy, hydroxy, halogen and trifluoromethyl, and is especially phenyl.

Acyl is, for example, lower alkanoyl.

Salts of compounds of formula I are especially pharmaceutically acceptable salts, for example acid addition salts with suitable mineral acids, such as hydrohalic acids, sulfuric acid or phosphoric acid, for example hydrochlorides, hydrobromides, sulfates, hydrogen sulfates or phosphates, salts with suitable aliphatic or aromatic sulfonic acids or N-substituted sulfamic acids, for example methanesulfonates, benzenesulfonates, p-toluene-sulfonates or N-cyclohexylsulfamates (cyclamates), or salts with strong organic carboxylic acids, such as lower alkanecarboxylic acids, or aliphatic dicarboxylic acids which may be unsaturated or hydroxylated, for example acetates, oxalates, malonates, maleates, fumarates, malates, tartrates or citrates.

For isolation or purification purposes it is also possible to use pharmaceutically unacceptable salts. Only the pharmaceutically acceptable non-toxic salts are used therapeutically, and those salts are therefore preferred.

The compounds of formula I and their pharmaceutically acceptable salts have valuable pharmacological properties. In particular, they exhibit a pronounced inhibitory action on the biosynthesis of interleukin-1 (IL-1). IL-1 belongs to the class of the proinflammatory proteins and plays an important part, for example, in prostaglandin synthesis, in the synthesis of neutral proteases by fibroplasts, synovial cells and chondrocytes, in the activation of endothelial cells and in the induction of other proinflammatory cytokines, such as the α-tumour necrosis factor (TNF) and interleukin-6 (IL-6). Furthermore, it stimulates bone resorption, regulates the body temperature of warm-blooded animals and regulates inter alia the development, activation, differentiation and proliferation of lymphocytes. Of particular importance therapeutically is the inhibitory action of the compounds of formula I and their pharmaceutically acceptable salts on the biosynthesis of IL-1, TNF and IL-6.

This can be demonstrated in vitro, for example, on lipopolysaccharide-stimulated (LPS-stimulated) human monocytes according to C. Rordorf-Adam et al., Drugs Exptl. Clin. Res. XV, 355–362 (1989) in a concentration range upwards from approximately 1 μmol, and in vivo in mice by means of the inhibition of the LPS-induced formation of serum amyloid P (SAP) at an $ED_{50}$ of approximately from 1 to 15 mg/kg p.o., and in rats by means of the reduction in the artificial fever produced by LPS at an $ED_{50}$ of approximately from 0.05 to 3.5 mg/kg p.o.

On account of those properties, the compounds of formula I and their pharmaceutically acceptable salts are excellently suitable for the therapeutic treatment of disorders in which excess production of IL-1 plays a causal or aggravating role, such as inflammatory and degenerative disorders of the joints, for example rheumatoid arthritis, osteoarthritis, psoriatic or infectious arthritis, of Reiter syndrome, of gout and traumatic arthritis, and of other acute or chronic inflammations, for example of inflammatory intestinal disorders, of meningitis, skin disorders, such as psoriasis, pemphigus vulgaris and the like, of allergic skin reactions, atherosclerosis and autoimmune disorders, such as diabetes (type 1) and thyroiditis.

Examples of other disorders in which excess production of IL-1 plays a causal or aggravating role are: disturbances in the regulation of bone metabolism, for example Paget's disease, osteoporosis, periodontitis or malignancies; or endotoxic shock, for example associated with fever, hypotension and fulminant liver failure.

In addition, the compounds of formula I and their pharmaceutically acceptable salts have a pronounced analgesic action which may be demonstrated, for example, by means of the inhibition of the phenyl-p-benzoquinone-induced writhing syndrome in mice, for example in a test arrangement based on that of Hendershot and Forsaith, J. Pharmacol. Exp. Therap. 125, 237 (1959) with an $ED_{50}$ of approximately from 1 to 30 mg/kg p.o.

The compounds of formula I and their pharmaceutically acceptable salts may accordingly be used also as active ingredients in analgesic medicaments for the treatment of pain of various origins, especially as peripheral analgesics.

The invention relates preferably to compounds of formula I wherein $R_1$ is hydrogen, lower alkyl, lower alkoxy-lower alkyl, lower alkoxy-lower alkoxy-lower alkyl; phenyloxy-lower alkyl or phenyl-lower alkoxy-lower alkyl, the phenyl group in each of the two last-mentioned radicals being unsubstituted or substituted by lower alkyl, trifluoromethyl, lower alkoxy, halogen and/or by hydroxy; N-lower alkylamino-lower alkyl or N,N-di-lower alkylamino-lower alkyl, $R_2$ is lower alkenoyl, (carboxy or lower alkoxycarbonyl)-lower alkenoyl, halo-lower alkanoyl, amino-lower alkanoyl, N-lower alkylamino-lower alkanoyl, N-[(carboxy or lower alkoxycarbonyl)-lower alkylamino]-lower alkanoyl, N,N-di-lower alkylamino-lower alkanoyl, $C_4$–$C_6$-lower alkyleneamino-lower alkanoyl, morpholino-lower alkanoyl, thiomorpholino-lower alkanoyl; piperazino-lower alkanoyl, the piperazino radical being unsubstituted or substituted in the 4-position by lower alkyl or by lower alkanoyl; hydroxy-lower alkanoyl, lower alkoxy-lower alkanoyl, lower alkanoyloxy-lower alkanoyl, lower alkylthio-lower alkanoyl, lower alkylsulfinyl-lower alkanoyl, lower alkylsulfonyl-lower alkanoyl; phenylthio-lower alkanoyl, phenylsulfinyl-lower alkanoyl or phenylsulfonyl-lower alkanoyl, the phenyl group in each of the three last-mentioned radicals being unsubstituted or substituted by lower alkyl, lower alkoxy, halogen and/or by hydroxy; carboxy-lower alkanoyl, lower alkoxycarbonyl-lower alkanoyl, carbamoyl-lower alkanoyl, N-lower alkylcarbamoyl-lower alkanoyl, N,N-di-lower alkylcarbamoyl-lower alkanoyl, cyano-lower alkanoyl, carbamoyl, N-lower alkylcarbamoyl, N,N-di-lower alkylcarbamoyl, carboxycarbonyl, lower alkoxycarbonylcarbonyl, (carbamoyl, N-lower alkylcarbamoyl or N,N-di-lower alkylcarbamoyl)carbonyl, or, when $R_1$ is lower alkoxy-lower alkyl, lower alkoxy-lower alkoxy-lower alkyl, or phenyloxy-lower alkyl or phenyl-lower alkoxy-lower alkyl each unsubstituted or substituted as defined above, N-lower alkylamino-lower alkyl or N,N-di-lower alkylamino-lower alkyl, $R_2$ may also be hydrogen, lower alkanoyl, carboxy, lower alkoxycarbonyl or phenyl-lower alkoxycarbonyl, wherein the phenyl group is unsubstituted or substituted by lower alkyl, lower alkoxy, halogen and/or by hydroxy, $R_3$ and $R_4$ are each independently of the other hydrogen, lower alkyl, halogen, lower alkoxy or lower alkylthio, $R_5$ and $R_6$ are each independently of the other hydrogen, lower alkyl, halo-lower alkyl, lower alkoxy, lower alkylthio, halogen, amino, lower alkylamino, di-lower alkylamino or lower alkanoylamino, and X and Y are each independently of the other a direct bond, lower alkylene or lower alkenylene, and salts thereof.

The invention relates especially preferably to compounds of formula I wherein $R_1$ is hydrogen, lower alkyl, lower alkoxy-lower alkyl, lower alkoxy-lower alkoxy-lower alkyl, phenyloxy-lower alkyl, N-lower alkylamino-lower alkyl or N,N-di-lower alkylamino-lower alkyl, $R_2$ is lower alkenoyl, (carboxy or lower alkoxycarbonyl)-lower alkenoyl, halo-lower alkanoyl, N-lower alkylamino-lower alkanoyl, N-[(carboxy or lower alkoxycarbonyl)-lower alkylamino]-lower alkanoyl, N,N-di-lower alkylamino-lower alkanoyl, piperidino-lower alkanoyl, hydroxy-lower alkanoyl, lower alkoxy-lower alkanoyl, lower alkanoyloxy-lower alkanoyl, lower alkylthio-lower alkanoyl, lower alkylsulfinyl-lower alkanoyl, lower alkylsulfonyl-lower alkanoyl, phenylthio-lower alkanoyl, phenylsulfinyl-lower alkanoyl, phenylsulfonyl-lower alkanoyl, carboxy-lower alkanoyl, lower alkoxy-carbonyl-lower alkanoyl, N,N-di-lower alkylcarbamoyl or lower alkoxycarbonylcarbonyl, or, when $R_1$ is lower alkoxy-lower alkyl or N,N-di-lower alkylamino-lower alkyl, $R_2$ may also be hydrogen, lower alkanoyl, lower alkoxycarbonyl or phenyl-lower alkoxycarbonyl, $R_3$ and $R_4$ are each independently of the other hydrogen, lower alkyl, halogen, lower alkoxy or lower alkylthio, $R_5$ and $R_6$ are each independently of the other hydrogen, lower alkyl, trifluoromethyl, lower alkoxy, lower alkylthio, halogen or di-lower alkylamino, and X and Y are each independently of the other a direct bond, lower alkylene or lower alkenylene, and salts thereof.

The invention relates very especially preferably to compounds of formula I wherein $R_1$ is hydrogen, lower alkyl or lower alkoxy-lower alkyl, $R_2$ is lower alkenoyl or halo-lower alkanoyl, or, when $R_1$ is lower alkoxy-lower alkyl, $R_2$ may also be hydrogen, $R_3$ and $R_4$ are each hydrogen, $R_5$ is chlorine, $R_6$ is hydrogen, X is a direct bond and Y is 1,2-ethylene, and pharmaceutically acceptable salts thereof.

The invention relates especially also to the compounds of formula Ia

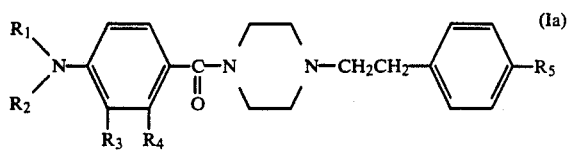

wherein $R_1$ is hydrogen, lower alkyl or lower alkoxy-lower alkyl, $R_2$ is lower alkenoyl, or lower alkanoyl substituted by halogen, di-lower alkylamino, 4- to 6-membered lower alkyleneamino or by lower alkylthio, or, when $R_1$ is lower alkoxy-lower alkyl, $R_2$ may also be hydrogen, $R_3$ and $R_4$ are each independently of the other hydrogen, lower alkyl, chlorine, fluorine or bromine, and $R_5$ is lower alkylthio, chlorine, fluorine or bromine, and salts thereof.

The invention relates especially to compounds of formula Ia wherein $R_1$ is hydrogen, lower alkyl or lower alkoxy-lower alkyl, $R_2$ is lower alkanoyl substituted by halogen, lower alkylthio, lower alkylsulfinyl or by lower alkylsulfonyl, or, when $R_1$ is lower alkoxy-lower alkyl, $R_2$ may also be hydrogen, $R_3$ and $R_4$ are each independently of the other hydrogen, lower alkyl, chlorine, fluorine or bromine, and $R_5$ is lower alkylthio, chlorine, fluorine or bromine, and their salts.

The invention relates more especially to compounds of formula Ia wherein $R_1$ is hydrogen, $C_1$-$C_4$alkyl or $C_1$-$C_4$alkoxy-$C_2$-$C_4$alkyl, $R_2$ is $C_3$-$C_7$alkenoyl, chloro-$C_2$-$C_4$alkanoyl, $C_1$-$C_4$alkylthio-, $C_1$-$C_4$alkylsulfinyl- or $C_1$-$C_4$alkylsulfonyl-$C_2$-$C_4$alkanoyl, or, when $R_1$ is $C_1$-$C_4$alkoxy-$C_2$-$C_4$alkyl, $R_2$ may also be hydrogen, $R_3$ and $R_4$ are each independently of the other hydrogen, $C_1$-$C_4$alkyl, fluorine or chlorine, and $R_5$ is chlorine, and pharmaceutically acceptable salts thereof.

The invention relates most especially to compounds of formula I wherein $R_1$ is hydrogen, methyl, ethyl or 2-isopropyloxyethyl, $R_2$ is prop-2-enoyl, chloroacetyl, 3-chloropropionyl, methylthioacetyl or ethylthioacetyl, $R_3$ and $R_4$ are each hydrogen, methyl, fluorine or chlorine, and $R_5$ is chlorine, and pharmaceutically acceptable salts thereof.

The invention relates specifically to the compounds of formula I mentioned in the Examples and their salts, especially their pharmaceutically acceptable salts.

The process for the preparation of the compounds of formula I is based on methods known per se and comprises, for example, a) reacting a compound of formula II

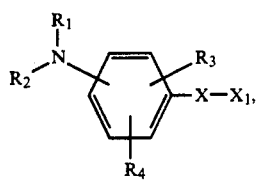

wherein $X_1$ is carboxy or reactive functionally modified carboxy, or a salt thereof, with a compound of formula III

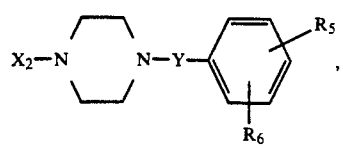

wherein $X_2$ is hydrogen or an amino-protecting group, or b) reacting a compound of formula IV

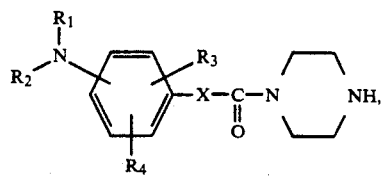

or a salt thereof, with a compound of formula V

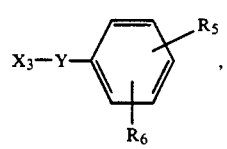

wherein $X_3$ is hydroxy or reactive esterified hydroxy, or c) cyclising a compound of formula VI

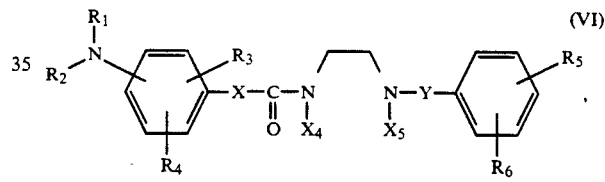

wherein one of the radicals $X_4$ and $X_5$ is hydrogen and the other is a group of the formula —$CH_2$—$CH_2$—$X_3$ (VIa) and $X_3$ is hydroxy or reactive esterified hydroxy, or d) oxidising a compound of formula VII

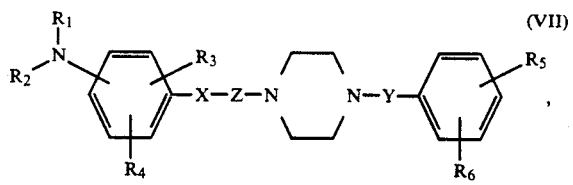

wherein Z is a group that can be oxidised to form carbonyl, or e) introducing the radical $R_2$ ($R_2 \neq H$) into a compound of formula VIII

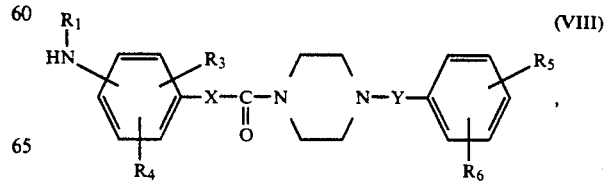

or f) for the preparation of compounds wherein $R_1$ is lower alkoxy-lower alkyl, introducing the radical $R_1$ into a compound of formula IX

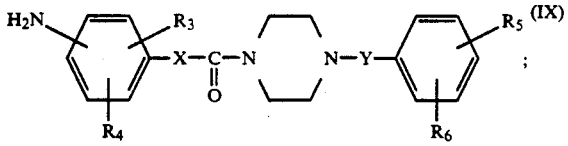

and in each case, if desired, converting a compound obtainable according to the process or in another manner into a different compound of formula I, separating a mixture of isomers obtainable according to the process into the components, converting a free compound of formula I obtainable according to the process into a salt and/or converting a salt obtainable according to the process into the free compound of formula I or into a different salt.

The reactions described hereinbefore and hereinafter are carried out in a manner known per se, for example in the absence or, customarily, in the presence of a suitable solvent or diluent or a mixture thereof, the reaction being carried out, as required, with cooling, at room temperature or with heating, for example in a temperature range of from approximately −78° to the boiling temperature of the reaction medium, preferably from approximately −10° to approximately 150° C., and, if necessary, in a closed vessel, under pressure, in an inert gas atmosphere and/or under anhydrous conditions.

In the starting materials, the basic centre may be, for example, in the form of an acid addition salt, for example with an acid mentioned above in connection with salts of compounds of formula I, while starting materials of formula II wherein $X_1$ is carboxy can form salts with bases. Suitable salts with bases are, for example, corresponding alkali metal or alkaline earth metal salts, for example sodium, potassium or magnesium salts, pharmaceutically acceptable transition metal salts, such as zinc or copper salts, or salts with ammonia or organic amines, such as cyclic amines, such as mono-, di- or tri-hydroxy-$C_1$-$C_7$alkylamines, hydroxy-$C_1$-$C_7$alkyl-$C_1$-$C_7$alkylamines or polyhydroxy-$C_4$-$C_7$alkylamines. Cyclic amines are, for example, morpholine, thiomorpholine, piperidine or pyrrolidine. There come into consideration as mono-$C_1$-$C_7$alkylamines, for example, ethyl- or tert-butyl-amine; as di-$C_1$-$C_7$alkylamines, for example, diethyl- or diisopropyl-amine; and as tri-$C_1$-$C_7$alkylamines, for example, trimethyl- or triethyl-amine. Corresponding hydroxy-$C_1$-$C_7$alkylamines are, for example, mono-, di- or tri-ethanol-amines, and hydroxy-$C_1$-$C_7$alkyl-$C_1$-$C_7$alkylamines are, for example, N,N-dimethylamino-or N,N-diethylamino-ethanol, and glucosamine is an example of a polyhydroxy-$C_6$alkylamine.

Reactive functionally modified carboxy $X_1$ is, for example, esterified, especially reactive esterified, carboxy, anhydridised carboxy or amidated carboxy.

Esterified carboxy is, for example, unsubtituted or substituted $C_1$-$C_7$alkoxycarbonyl, such as ethoxycarbonyl, but is preferably reactive esterified carboxy, for example vinyloxy-carbonyl which may be additionally activated, for example, by $C_1$-$C_7$alkoxy or by unsubstituted or substituted carbamoyl, such as 1-$C_1$-$C_7$alkoxy-, for example 1-ethoxy-vinyloxy-carbonyl, or 2-(N-$C_1$-$C_7$alkylcarbamoyl)-, for example 2-(N-ethylcarbamoyl)-vinyloxy-carbonyl, as well as phenoxy- or thiophenoxy-carbonyl each of which is unsubstituted or substituted, for example by nitro, halogen, $C_1$-$C_7$alkanesulfonyl or by phenylazo, such as 4-nitro-, 2,4,5-trichloro-, pentachloro-, 4-methanesulfonyl-, or 4-phenylazo-phenoxy-carbonyl, or thiophenoxy- or 4-nitrothiophenoxy-carbonyl, and also activated methoxy-carbonyl, for example methoxycarbonyl substituted by cyano or by free or esterified carboxy, especially cyanomethoxycarbonyl. Reactive esterified carboxy may also be 1,1- or 1,3-disubstituted 2-isoureidocarbonyl, such as 1,1-di-lower alkyl-, 1,1-diaryl- or 1,1-diaryl-$C_1$-$C_7$alkyl-2-isoureidocarbonyl, for example 1,1-diethyl-, 1,1-diphenyl- or 1,1-dibenzyl-2-isoureidocarbonyl, or 1,3-dicycloalkyl-, for example 1,3-dicyclohexyl-2-isoureidocarbonyl, or N-$C_2$-$C_7$alkyleneaminooxycarbonyl, such as N-piperidinyloxycarbonyl, and also N-imidooxycarbonyl, for example N-succinimidooxy- or N-phthalimidooxycarbonyl.

Anhydridised carboxy is to be understood as meaning, for example, unbranched or branched $C_1$-$C_7$alkoxycarbonyloxycarbonyl, such as ethoxy- or isobutyloxy-carbonyloxycarbonyl, halocarbonyl, such as chlorocarbonyl, azidocarbonyl, halophosphoryloxycarbonyl, such as dichlorophosphoryloxycarbonyl, or $C_1$-$C_7$alkanoyloxycarbonyl that is unsubstituted or substituted, for example by halogen or by aryl, such as pivaloyloxy-, trifluoroacetyloxy- or phenylacetoxy-carbonyl.

Reactive amidated carboxy is, for example, 1-imidazolyl- or 1-pyrazolyl-carbonyl each of which is unsubstituted or substituted, for example by $C_1$-$C_7$alkyl, such as 3,5-dimethylpyrazolylcarbonyl.

An amino-protecting group $X_2$ is, for example, acyl, such as $C_1$-$C_7$alkanoyl, for example formyl or acetyl, halocarbonyl, such as chlorocarbonyl, and also unsubstituted or substituted aryl- or heteroaryl-sulfonyl, such as 2-pyridyl- or 2-nitrophenyl-sulfonyl.

Within the context of the description of the processes given hereinbefore and hereinafter, unless defined otherwise, reactive esterified hydroxy, for example $X_3$, is especially hydroxy esterified by a strong inorganic acid or organic sulfonic acid, for example halogen, such as chlorine, bromine or iodine, sulfonyloxy, such as hydroxysulfonyloxy, halosulfonyloxy, for example fluorosulfonyloxy, $C_1$-$C_7$alkanesulfonyloxy that is unsubstituted or substituted, for example by halogen, for example methane- or trifluoromethane-sulfonyloxy, $C_3$-$C_7$-cycloalkanesulfonyloxy, for example cyclohexanesulfonyloxy, or benzenesulfonyloxy that is unsubstituted or substituted, for example by $C_1$-$C_7$alkyl or by halogen, for example p-bromophenyl- or p-toluene-sulfonyloxy.

If, for example, bases are used in the reactions described hereinbefore and hereinafter, then there are suitable, for example, unless indicated otherwise, alkali metal hydroxides, hydrides, amides, alkanolates, carbonates, triphenylmethylides, di-$C_1$-$C_7$alkylamides, amino-$C_1$-$C_7$alkylamides or $C_1$-$C_7$alkylsilylamides, naphthylamines, $C_1$-$C_7$alkylamines, basic heterocycles, ammonium hydroxides and carbocyclic amines. There may be mentioned by way of example lithium hydroxide, sodium hydroxide, sodium hydride, sodium amide, sodium ethanolate, potassium tert-butanolate, potassium carbonate, lithium triphenylmethylide, lithium diisopropylamide, potassium 3-(aminopropyl)amide, potassium bis(trimethylsilyl)amide, dimethylaminonaphthalene, di- or tri-ethylamine, pyridine, benzyltrimethylammonium hydroxide, 1,5-diazabicyclo[4.3.0]non-5-ene (DBN) and 1,8-diazabicyclo[5.4.0]undec-7-ene (DBU).

Variant a): The N-acylation according to the process is carried out in a manner known per se, if necessary in the presence of a condensation agent, especially a basic condensation agent. Suitable bases are, for example, representatives of the bases mentioned above. Frequently the basicity of the compound of formula III is sufficient.

When $X_1$ is carboxy, there are formed initially, for example, the corresponding ammonium salts, which can be dehydrated by heating or by treatment with suitable dehydrating agents (as condensation agents), such as carbodiimides, for example N,N'-di-lower alkyl- or N,N'-dicycloalkyl-carbodiimide, such as N,N'-diethyl-, N,N'-diisopropyl- or N,N'-dicyclohexyl-carbodiimide, advantageously with the addition of N-hydroxysuccinimide, or of 1-hydroxybenzotriazole which is unsubstituted or substituted, for example by halogen, lower alkoxy or by lower alkyl, or of N-hydroxy-5-norbornene-2,3-dicarboxamide or N,N-carbonyldiimidazole. When carbodiimides are used, the corresponding 1-isoureidocarbonyl compounds, for example, may also be formed intermediately. There may be used as water-binding condensation agents also N-ethoxycarbonyl-2-ethoxy-1,2-dihydroquinoline, phosphoryl-cyanamides or -azides, such as diethylphosphorylcyanamide or diphenylphosphorylazide, triphenylphosphine disulfide or 1-lower alkyl-2-halopiperidinium halides, such as 1-methyl-2-chloropyridinium iodide.

Some of the starting materials used in this process variant are known, or they can be prepared according to processes known per se.

For the preparation of compounds of formula II wherein $X_1$ is unsubstituted or substituted $C_1$-$C_7$alkoxycarbonyl, it is possible in customary manner to use the free acid ($X_1$=carboxy) or an acid anhydride ($X_1$ is, for example, halocarbonyl) as starting material and to react it, for example, with the corresponding alcohol, which may if necessary be in reactive form, for example a $C_1$-$C_7$alkyl halide. The preparation of compounds of formula II wherein $X_1$ is optionally additionally activated vinyloxycarbonyl may be effected, for example, by transesterification of a $C_1$-$C_7$alkyl ester with vinyl acetate (activated vinyl ester method), by reaction of the free acid of compounds of formula II with lower alkoxyacetylene (e.g. ethoxyacetylene method) or, analogously to the Woodward method, with a 1,2-oxazolium salt. Compounds of formula II containing unsubstituted or substituted phenoxy- or thiophenoxycarbonyl can be prepared, for example, starting from the free acid by the carbodiimide method by reaction with the corresponding (thio)phenol. Likewise starting from the free acid of formula II it is possible to obtain compounds of formula II wherein $X_1$ is activated methoxycarbonyl or 1,1- or 1,3-disubstituted 2-isoureidocarbonyl, for example by reaction with a haloacetonitrile, such as chloroacetonitrile, (cyanomethyl ester method) or with a carbodiimide or cyanamide (carbodiimide or cyanamide method). The preparation of N-$C_2$-$C_7$alkylene-aminooxycarbonyl or N-imidooxycarbonyl compounds of formula II can be carried out, for example, using the free acid of formula II, from corresponding N-hydroxy compounds with the aid of carbodiimides by the activated N-hydroxy ester method. For the preparation of compounds of formula II wherein $X_1$ is unbranched or branched $C_1$-$C_7$alkoxycarbonyloxycarbonyl, halophosphoryloxycarbonyl or unsubstituted or substituted $C_1$-$C_7$-alkanoyloxycarbonyl, it is possible to use as starting material, for example, the free acid of formula II, which can be treated, for example, with a corresponding halide, such as an unsubstituted or substituted $C_1$-$C_7$alkylcarbonic acid halide (mixed O-carbonic acid anhydrides method), a phosphorus oxyhalide (e.g. phosphorus oxychloride method) or an unsubstituted or substituted $C_1$-$C_7$alkanoyl halide (mixed carboxylic acid halides method). Azidocarbonyl compounds of formula II are obtainable, for example, by treatment of corresponding hydrazides with nitrous acid (azide method). For the preparation of compounds of formula II wherein $X_1$ is unsubstituted or substituted 1-imidazolylcarbonyl or 1-pyrazolylcarbonyl, the free acid of formula II is reacted, for example, with di(1-imidazolyl)carbonyl (imidazolide method), or the corresponding hydrazide is reacted, for example, with a corresponding 1,3-diketone (pyrazolide method).

Variant b): The radical $X_3$ is especially reactive esterified hydroxy, for example halogen, such as chlorine.

The N-alkylation according to the process is carried out in a manner known per se, if necessary in the presence of a base, for example one of those mentioned above.

Some of the starting materials used in this process variant are known, or they can be prepared in a manner known per se.

For example, the starting material of formula IV can be prepared by reacting a compound of formula II, or a salt thereof, wherein $X_1$ is carboxy or reactive functionally modified carboxy, with a compound of formula IVa

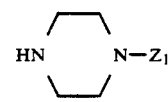

(IVa)

or with a salt thereof, wherein $Z_1$ is hydrogen or an amino-protecting group, such as benzyl, in the manner described in variant a) and, if necessary, removing the amino-protecting group, for example benzyl, by customary hydrogenolysis.

Variant c): The cyclisation (intramolecular N-alkylation) according to the process is carried out in a manner known per se, if necessary in the presence of a condensation agent, especially a basic condensation agent. There are used as bases, for example, those mentioned above.

$X_3$ is here especially reactive esterified hydroxy, preferably halogen, such as chlorine.

The starting material can be prepared in a manner known per se, for example starting from a compound of formula II, or a salt thereof, wherein $X_1$ is carboxy or reactive functionally modified carboxy, which is first reacted with a compound of formula

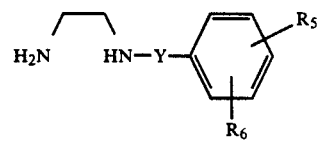

(VIb)

analogously to variant a). In the next reaction step, the resulting compound is reacted with a compound of the formula $X_3$—$CH_2$—$CH_2$—$X_3$ (VIc) under N-alkylating conditions according to variant b).

Variant d): A group Z that can be oxidised to form —CO— is especially —CH$_2$—. The oxidation of corresponding compounds of formula VII is carried out by means of a suitable oxidising agent, there preferably being used a tetra-C$_1$-C$_4$alkylammonium permanganate that is unsubstituted or substituted, for example by a phenyl radical, especially benzyltriethylammonium permanganate.

The starting material of formula VII is prepared in a manner known per se, for example starting from a compound of formula III wherein X$_2$ is hydrogen, which is reacted under the N-alkylating conditions described in variant b) with a compound of formula VIIa

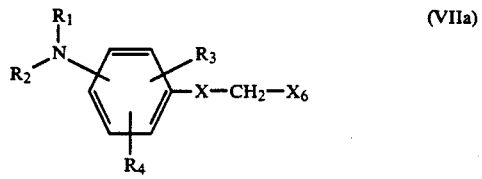

wherein X$_6$ is hydroxy or, especially, reactive esterified hydroxy, especially halogen, such as chlorine or bromine.

Variant e): The introduction of lower alkenoyl or electronegatively substituted lower alkanoyl (N-acylation) is carried out in customary manner, if necessary in the presence of a condensation agent, especially a basic condensation agent. There are suitable as bases, for example, representatives of the bases mentioned above.

Varient f): The introduction of lower alkoxy-lower alkyl R$_1$ (N-alkoxyalkylation) is carried out in customary manner, if necessary in the presence of a condensation agent, especially a basic condensation agent. There are suitable as bases, for example, representatives of the bases mentioned above.

A compound according to the invention obtainable according to the process or in another manner can be converted in a manner known per se into a different compound according to the invention.

In compounds according to the invention wherein R$_1$ is lower alkoxy-lower alkyl and R$_2$ is hydrogen, the amino group can be N-acylated in the manner indicated above under varient a), b) or e). Likewise, a compound of formula I wherein R$_1$ is hydrogen and R$_2$ is lower alkenoyl or electronegatively substituted lower alkanoyl can be N-lower alkylated or N-substituted by lower alkoxy-lower alkyl in the manner indicated for process variant f). The N-lower alkylation can also be carried out by reduction analogously to the Leuckart-Wallach (or Eschweiler-Clarke) reaction from carbonyl compounds, for example using formic acid as reducing agent.

Resulting salts can be converted into the free compounds in a manner known per se, for example by treatment with a base, such as an alkali metal hydroxide, a metal carbonate or hydrogen carbonate, or ammonia, or another salt-forming base mentioned at the beginning, or with an acid, such as a mineral acid, for example with hydrochloric acid, or another salt-forming acid mentioned at the beginning.

Resulting salts can be converted into different salts in a manner known per se; acid addition salts can be converted, for example, by treatment with a suitable metal salt, such as a sodium, barium or silver salt, of a different acid in a suitable solvent in which an inorganic salt that forms is insoluble and therefore is eliminated from the reaction equilibrium, and basic salts can be converted by freeing the free acid and converting it into a salt again.

The compounds of formula I, including their salts, can also be obtained in the form of hydrates or include the solvent used for crystallisation.

In view of the close relationship between the novel compounds in free form and in the form of their salts, hereinbefore and hereinafter any reference to the free compounds or their salts is to be understood as including the corresponding salts or free compounds, as appropriate and expedient.

The invention relates also to those forms of the process in which a compound obtainable as intermediate at any stage of the process is used as starting material and the remaining steps are carried out, or in which a starting material is used in the form of a salt or, especially, is formed under the reaction conditions.

The invention relates also to the novel starting materials which were developed specifically for the preparation of the compounds according to the invention, especially to those starting materials that result in the compounds of formula I characterised at the beginning as being preferred, to processes for their preparation, and to their use as intermediates.

The novel compounds of formula I can be used, for example, in the form of pharmaceutical compositions that comprise a therapeutically effective amount of the active ingredient, optionally together with inorganic or organic, solid or liquid, pharmaceutically acceptable carriers, which are suitable for enteral, e.g. oral, or parenteral administration. There are used, for example, tablets or gelatin capsules that comprise the active ingredient together with diluents, for example lactose, dextrose, saccharose, mannitol, sorbitol, cellulose, and/or lubricants, for example silica, talc, stearic acid or salts thereof, such as magnesium or calcium stearate, and/or polyethylene glycol. Tablets can also comprise binders, for example magnesium aluminum silicate, starches, such as corn, wheat, rice or arrowroot starch, gelatin, tragacanth, methylcellulose, sodium carboxymethylcellulose and/or polyvinylpyrrolidone, and, if desired, disintegrators, for example starches, agar, alginic acid or a salt thereof, for example sodium alginate, and/or effervescent mixtures, or absorbents, colouring agents, flavourings and sweetners. The novel compounds of formula I can also be used, for example, in the form of parenterally administrable compositions or in the form of infusion solutions. Such solutions are preferably isotonic aqueous solutions or suspensions which, for example in the case of lyophilised compositions that comprise the active ingredient on its own or together with a carrier, for example mannitol, can be prepared before use. The pharmaceutical compositions may be sterilised and/or may comprise excipients, for example preservatives, stabilisers, wetting agents and/or emulsifiers, solubilisers, salts for regulating the osmotic pressure and/or buffers. The pharmaceutical compositions in question, which, if desired, may comprise further pharmacologically active substances, are prepared in a manner known per se, for example by means of conventional mixing, granulating, confectioning, dissolving or lyophilising processes, and comprise approximately from 0.1% to 100%, especially from approximately 1% to approximately 50%, in the case of lyophilisates up to approximately 100%, active ingredient.

The invention relates also to the use of the compounds of formula I, preferably in the form of pharmaceutical compositions. The dosage may depend upon various factors, such as the mode of administration and the species, age and/or individual condition. The doses to be administered daily are, in the case of oral administration, from approximately 0.25 to approximately 10 mg/kg, and in the case of warm-blooded animals having a body weight of approximately 70 kg, they are preferably from approximately 20 mg to approximately 500 mg.

The following Examples serve to illustrate the invention; temperatures are given in degrees Celsius and pressures in mbar. The following abbreviations are used: RT=room temperature, ET=external temperature, IT=internal temperature, ether=diethyl ether, (BOC$_2$)O=di-tert-butyl dicarbonate.

EXAMPLE 1

3.4 g of 1-(4-aminobenzoyl)-4-[2-(4-chlorophenyl)ethyl]piperazine and 2.6 g of 2-isopropyloxyethyl p-toluenesulfonate are suspended in 30 ml of toluene and heated to boiling point. The clear solution so obtained is boiled under reflux for 17 hours and then concentrated by evaporation. Water is added to the residue, and the mixture is rendered alkaline with concentrated sodium hydroxide solution and extracted by shaking with methylene chloride. The crude oil is chromatographed over silica gel and crystallised in the form of the hydrochloride from acetone, yielding 1-{4-[N-(2-isopropyloxyethyl)amino]benzoyl}-4-[2-(4-chlorophenyl)ethyl]piperazine hydrochloride having a melting point of 184°–185°.

The starting material is prepared as follows:

37.2 g of 1-(4-nitrobenzoyl)-4-[2-(4-chlorophenyl)ethyl]piperazine are reduced at room temperature in 370 ml of tetrahydrofuran in the presence of 20 g of Raney nickel. The filtered reaction solution is concentrated by evaporation and the resulting oil is crystallised from isopropanol/petroleum ether, yielding 30 g of 1-(4-aminobenzoyl)-4-[2-(4-chlorophenyl)ethyl]piperazine having a melting point of 111°–112°.

The 1-(4-nitrobenzoyl)-4-[2-(4-chlorophenyl)ethyl]piperazine is prepared from 4-nitrobenzoic acid and 1-[(4-chlorophenyl)ethyl]piperazine in N,N-dimethylformamide in the presence of N,N-carbonylimidazole. It melts at 109°–110°.

EXAMPLE 2

69.8 g of 1-{4-[N-(2-isopropyloxyethyl)-N-tert-butyloxycarbonylamino]benzoyl}-4-[2-(4-chlorophenyl)ethyl]piperazine are dissolved in 900 ml of methylene chloride, and 600 ml of trifluoroacetic acid are added. The dark solution is left to stand overnight at room temperature and is concentrated by evaporation in vacuo. Ice-cold water is added to the residue and the mixture is rendered alkaline with ammonia and extracted by shaking with methylene chloride. The dark oil is chromatographed over silica gel. The methylene chloride/acetone eluate (7:3) is concentrated by evaporation and dried in vacuo. The oily 1-{4-[N-(2-isopropyloxyethyl)amino]benzoyl}-4-[2-(4-chlorophenyl)ethyl]piperazine slowly solidifies; m.p. 61°–63°.

The starting material is prepared as follows: 38 g of 4-(N-acetylamino)benzoyl-4-[2-(4-chlorophenyl)ethyl]piperazine (see EP-A-250 361) are dissolved in 400 ml of acetonitrile. 1.2 g of 4-dimethylaminopyridine dissolved in 20 ml of acetonitrile are added thereto, and then 24.5 g of (BOC$_2$)O in 100 ml of acetonitrile are added dropwise. The mixture is stirred for 6 hours at RT, and then a further 5 g of (BOC$_2$)O are added. After 5 minutes at 35° and one hour at RT, 20 g of 2-diethylaminoethylamine are added. The mixture is stirred overnight at RT, the 1-{4-[N-(acetyl)-N-tert-butyloxycarbonylamino]benzoyl}-4-[2-(4-chlorophenyl)ethyl]piperazine formed intermediately being cleaved to form 1-[N-(tert-butyloxycarbonylamino)benzoyl]-4-[2-(4-chlorophenyl)ethyl]piperazine. It is isolated by concentration by evaporation, extraction with ethyl acetate and crystallisation from ether. It melts at 129°–131°.

4.4 g of 1-[N-(tert-butyloxycarbonylamino)benzoyl]-4-[2-(4-chlorophenyl)ethyl]piperazine are dissolved in 15 ml of DMSO. 0.67 g of powdered KOH is added thereto. The mixture is stirred for 15 minutes at RT, and then a solution of 3 g of O-(2-isopropyloxyethyl) tosylate in 10 ml of DMSO is added dropwise within a period of 5 minutes. The mixture is stirred for 7 hours at RT and for 3 hours at 60°–70°. The solution is left to stand overnight at RT. It is poured onto 150 ml of water, decanted off and again poured onto 150 ml of water. The oil that separates out is extracted with ethyl acetate, washed with water until neutral and concentrated by evaporation, yielding 1-{4-[N-(2-isopropyloxyethyl)-N-tert-butyloxycarbonylamino]benzoyl}-4-[2-(4-chlorophenyl)ethyl]piperazine having a melting point of 182°–184°.

EXAMPLE 3

22 g of 1-{4-[N-(2-isopropyloxyethyl)amino]benzoyl}-4-[2-(4-chlorophenyl)ethyl]piperazine (Example 2) and 20.7 g of potash are introduced into 650 ml of toluene, and the mixture is kept at 45° for 15 minutes. At that temperature and with stirring, a solution of 7.1 g of chloroacetyl chloride in 30 ml of toluene is added dropwise. The mixture is stirred for 30 minutes at 45° and then stirring is continued at room temperature. The reaction solution is diluted with 500 ml of ethyl acetate and washed twice with 250 ml of water each time. The oil obtained after concentration by evaporation is chromatographed over silica gel and recrystallised in the form of the hydrochloride from acetone/ether, yielding 1-{4-[N-(2-isopropyloxyethyl)-N-chloroacetylamino]benzoyl}-4-[2-(4-chlorophenyl)ethyl]piperazine hydrochloride having a melting point of 146°–147°.

Treatment of the hydrochloride with ammonia yields the free base, which is extracted with dichloromethane. It is concentrated by evaporation and chromatographed over silica gel (eluant: ethyl acetate). The oily base is crystallised from isopropyl ether; m.p. 83°–84°.

To a solution of 4.83 g of the free base in 50 ml of ethanol there are added 1.06 g of fumaric acid in 70 ml of ethanol; after 3 days at RT, there are signs of crystallisation. The addition of a small amount of acetone and ether and standing for a further 2 days at RT and finally for 12 hours at 0° yield a suspension, which is filtered with suction. The residue is dried over KOH in a drying cabinet at 60°, yielding 1-{4-[N-(2-isopropyloxyethyl)-N-chloroacetylamino]benzoyl}-4-[2-(4-chlorophenyl)ethyl]piperazine fumarate having a melting point of 105°–107°.

EXAMPLE 4

In a manner analogous to that described in Examples 1 to 3, the following may also be prepared:

(a) 1-[4-(N-methyl-N-chloroacetylamino)benzoyl]-4-[2-(4-chlorophenyl)ethyl]piperazine; m.p. 113°–115°;

(b) 1-{4-[N-(3-methylbutyl)-N-chloroacetylamino]benzoyl}-4-[2-(4-chlorophenyl)ethyl]piperazine;

(c) 1-[2-chloro-4-(N-chloroacetylamino)benzoyl]-4-[2-(4-chlorophenyl)ethyl]piperazine;

(d) 1-[3-methoxy-4-(N-chloroacetylamino)benzoyl]-4-[2-(4-chlorophenyl)ethyl]piperazine;

(e) 1-{4-[N-(4-methylpentyl)-N-chloroacetylamino]benzoyl}-4-[2-(4-chlorophenyl)ethyl]piperazine; m.p. 90°–91°.

EXAMPLE 5

11 g of 1-(4-aminobenzoyl)-4-[2-(4-chlorophenyl)ethyl]piperazine and 5.7 g of 3-ethoxypropyl bromide are suspended in 150 ml of isopropanol and dissolved at 100°. 9.4 g of potash are added thereto, and the mixture is boiled under reflux for 20 hours. Concentration by evaporation and chromatography over silica gel yield an oil, which is crystallised from methylene chloride and petroleum ether, yielding 1-[4-(3-ethoxypropylamino)benzoyl]-4-[2-(4-chlorophenyl)ethyl]piperazine having a melting point of 87°–89°.

EXAMPLE 6

1.7 g of 1-(4-aminobenzoyl)-4-[2-(4-chlorophenyl)ethyl]piperazine and 0.55 g of triethylamine are introduced into 25 ml of methylene chloride. A solution of 0.6 g of chloroacetyl chloride is added dropwise thereto. The dark solution is left to stand overnight, diluted with 50 ml of methylene chloride, washed with 1N sodium hydroxide solution, dried over magnesium sulfate and concentrated by evaporation. The crystallisate so obtained is recrystallised from acetone, yielding 1-(4-chloroacetylaminobenzoyl)-4-[2-(4-chlorophenyl)ethyl]piperazine having a melting point of 146°–147°.

EXAMPLE 7

2.34 g of 1-[2-(4-chlorophenyl)ethyl]piperazine and 1.57 g of Hunig base (=N-ethyldiisopropylamine) are introduced into 40 ml of tetrahydrofuran. 2.36 g of 4-chloroacetylaminobenzoic acid chloride [see J. Med. Chem. 28 (1985) 910] are added thereto in small portions. After 30 minutes at 40°, the solution is concentrated by evaporation. The residue is chromatographed over silica gel, and recrystallisation is carried out from acetone, yielding 1-(4-chloroacetylaminobenzoyl)-4-[2-(4-chlorophenyl)ethyl]piperazine having a melting point of 146°–147°.

EXAMPLE 8

In a manner analogous to that described in Example 3, 1-{4-[N-chloroacetyl-N-methylamino]benzoyl}-4-[2-(4-methylmercaptophenyl)ethyl]piperazine having a melting point of 120°–121° is prepared from 1.6 g of 1-(4-methylaminobenzoyl)-4-[2-(4-methylmercaptophenyl)ethyl]piperazine by reaction with chloroacetyl chloride.

The starting material is prepared as follows: (a) 64.3 g of 4-chloroethylthiophenol are placed in a vessel with 13.3 g of dimethyl sulfate; with external cooling (IT<10°), 41 ml of NaOH (25%) are then slowly added dropwise. After approximately one hour, the external cooling is removed and the mixture is heated carefully and kept at 125° for 30 minutes. The cooled solution is extracted with ether and distilled, yielding 4-methylmercaptophenylethyl chloride; b.p. 94°–95°/0.1 mbar.

(b) Under nitrogen, 59.6 g of 4-methylmercaptophenylethyl chloride are heated with 75.7 g of 1-ethoxycarbonylpiperazine for 1.5 hours at 130°. A further 25.2 g of 1-ethoxycarbonylpiperazine are added thereto, and after 1.5 hours a further 25.2 g of 1-ethoxycarbonylpiperazine are added. After a total of 4.5 hours, the solution is poured onto ice-water, rendered strongly alkaline with concentrated NaOH and extracted with ether. Concentration by evaporation yields a mobile oil, which is purified by chromatography over silica gel (eluant: dichloromethane and dichloromethane/acetone 8:2). 90 g of the 1-[(4-methylmercaptophenyl)ethyl]-4-ethoxycarbonylpiperazine so obtained are boiled under reflux for 17 hours with 700 ml of concentrated HCl. The solution is diluted with ice-water, rendered alkaline with concentrated NaOH, extracted with ethyl acetate, concentrated by evaporation and recrystallised from ether/petroleum ether. The 1-[2-(4-methylmercaptophenyl)ethyl]piperazine melts at 52°–54°.

(c) The 1-(4-methylaminobenzoyl)-4-[2-(4-methylmercaptophenyl)ethyl]piperazine is prepared from 1.66 g of 4-methylaminobenzoic acid, 1.95 g of N,N-carbonyldiimidazole and 2.35 g of 1-[2-(4-methylmercaptophenyl)ethyl]piperazine in dimethylformamide at 85°. The base is purified via the hydrochloride (m.p. 185°, decomp.) and melts at 120°–121°.

EXAMPLE 9

In a manner analogous to that described in Example 3, 1-{4-[N-chloroacetyl-N-methylamino]benzoyl}-4-[2-(4-bromophenyl)ethyl]piperazine having a melting point of 127°–129° is prepared from 0.4 g of 1-(4-methylaminobenzoyl)-4-[2-(4-bromophenyl)ethyl]piperazine by reaction with chloroacetyl chloride.

The starting material is prepared as follows: (a) 1.9 g of N,N-carbonyldiimidazole are added to a solution, stirred at room temperature, of 1.6 g of p-N-methylaminobenzoic acid in 25 ml of anhydrous dimethylformamide. After approximately 15 minutes, the vigorous evolution of gas ceases. The mixture is heated to 60°, and after 5 minutes 1.7 g of 1-[2-(4-bromophenyl)ethyl]piperazine are added. The mixture is stirred for 45 minutes at an oil bath temperature of 80°–85°. 2N sodium hydroxide solution and water are added to the cooled solution, and the mixture is stirred. 1-[4-(N-methylamino)benzoyl]-4-[2-(4-bromophenyl)ethyl]piperazine crystallises out. It is filtered off with suction and washed with water; m.p. 93°–94°.

EXAMPLE 10

In a manner analogous to that described in Example 3, 1-{4-[N-ethyl-N-chloroacetylamino]benzoyl}-4-[2-(4-chlorophenyl)ethyl]piperazine having a melting point of 118°–120° is prepared from 1 g of 1-(4-ethylaminobenzoyl)-4-[2-(4-chlorophenyl)ethyl]piperazine (see European Patent Application No. 489 690, Example 23) by reaction with chloroacetyl chloride.

The starting material is prepared in a manner analogous to that described in Example 9a from 4-ethylaminobenzoic acid and 1-[2-(4-chlorophenyl)ethyl]piperazine. It melts at 99°–101°.

EXAMPLE 11

In a manner analogous to that described in Example 6, the oily 1-{4-[N-(2-isopropyloxyethyl)-N-chloroacetylamino]benzoyl}-4-[2-(4-chlorophenyl)ethyl]piperazine is prepared from 1.35 g of 1-[4-(2-isopropyloxyethyl)aminobenzoyl]-4-[2-(4-chlorophenyl)ethyl]piperazine by reaction with chloroacetyl chloride; IR (CH$_2$Cl$_2$): 1650 cm$^{-1}$ (broad); NMR (CDCl$_3$): 1.15 (t, 3H), 1.8 (m, 2H), 2.5 (m) and 2.6 (t) (together 6H), 2.8 (t, 2H), 3.4 (m, 6H), 3.85 (m, 6H), 7.15 (d, 2H), 7.3 (m, 4H), 7.5 ppm (d, 2H).

EXAMPLE 12

2.5 g of 4-ethylmercaptoacetylaminobenzoic acid are introduced into 30 ml of dimethylformamide, and 1.75 g of N,N-carbonyldiimidazole are added. The mixture is stirred for 10 minutes at room temperature. At 80°, 1.75 g of 1-[2-(4-chlorophenyl)ethyl]piperazine are added thereto. The mixture is stirred for a further 45 minutes at 80°. The reaction solution is concentrated by evaporation and the oil is chromatographed. The hydrochloride is recrystallised from ethanol/ether, yielding 1-[4-(ethylmercaptoacetylamino)benzoyl]-4-[2-(4-chlorophenyl)ethyl]piperazine hydrochloride having a melting point of 229°-231°.

The starting material is prepared as follows: (a) 55.2 g of thioglycolic acid are introduced into a round-bottomed flask and heated to 140°-150°. 54.8 g of 4-aminobenzoic acid are added thereto in portions. The mixture is kept at 150° for 2 hours, then is allowed to cool to 100°, 500 ml of 2N NaOH are added and the mixture is dissolved. The solution is filtered through Hyflo and acidified with 80 ml of concentrated HCl. The mixture is filtered off with suction, washed with water, dissolved while still wet in 800 ml of methanol and concentrated to approximately 600 ml. 4-Mercaptoacetylaminobenzoic acid having a melting point of 220°-222° crystallises out.

(b) 15 g of 4-mercaptoacetylaminobenzoic acid are dissolved in 450 ml of tetrahydrofuran, and 39.2 g of potash and 17.24 ml of ethyl iodide in 50 ml of tetrahydrofuran are added thereto. The mixture is stirred overnight and 200 ml of water and a small amount of 2N NaOH are added thereto. The cloudy solution is filtered, and the filtrate is acidified with concentrated HCl. The yellow crystals are filtered off with suction and recrystallised from isopropanol, yielding 4-ethylmercaptoacetylaminobenzoic acid having a melting point of 209°-211°.

EXAMPLE 13

In a manner analogous to that described in Example 12, and by subsequent S-oxidation if desired, for example with m-chloroperbenzoic acid, the following may also be prepared:

(a) 1-[4-(methylmercaptoacetylamino)benzoyl]-4-[2-(4-chlorophenyl)ethyl]piperazine;

(b) 1-[4-(methylsulfinylacetylamino)benzoyl]-4-[2-(4-chlorophenyl)ethyl]piperazine, and (c) 1-[4-(methylsulfonylacetylamino)benzoyl]-4-[2-(4-chlorophenyl)ethyl]piperazine.

EXAMPLE 14

In a manner analogous to that described in Examples 12 and 14a, 1-{4-[N-methyl-N-methylmercaptoacetylamino]benzoyl}-4-[2-(4-chlorophenyl)ethyl]-piperazine may be prepared.

EXAMPLE 14a 1.3 g of ethylmercaptoacetic acid are dissolved in 25 ml of N,N-dimethylformamide, and 2.3 g of N,N-carbonyldiimidazole are added. After 15 minutes at RT, the mixture is heated for 5 minutes at 90° ET. Then 3.5 g of 1-[4-(N-methylamino)benzoyl]-4-[2-(4-chlorophenyl)ethyl]piperazine (see European Patent Application No. 489 690, Example 9) are added thereto, and the reaction mixture is kept at 110° ET for 14 hours. The mixture is concentrated by evaporation and the oil is chromatographed over silica gel (eluant: dichloromethane/acetone 8:2). Treatment with alcoholic hydrochloric acid yields 1-{4-[N-methyl-N-ethylmercaptoacetylamino]benzoyl}-4-[2-(4-chlorophenyl)ethyl]-piperazine hydrochloride having a melting point of 163°-164°.

EXAMPLE 15

Analogously to Example 12, 1-[4-(acryloylamino)-benzoyl]-4-[2-(4-chlorophenyl)ethyl]piperazine having a melting point of 163°-165° is prepared from 3.8 g of 4-acryloylaminobenzoic acid [=4-(prop-2-en-1-on-1-ylamino)benzoic acid] and 4.4 g of 1-[2-(4-chlorophenyl)ethyl]piperazine.

EXAMPLE 16

2 g of 1-(4-aminobenzoyl)-4-[2-(4-chlorophenyl)ethyl]piperazine and 0.82 g of Hünig base are introduced into 40 ml of tetrahydrofuran, and a solution of 0.8 g of 3-chloropropionic acid chloride is added dropwise thereto. The solution is left to stand overnight. The resulting suspension is concentrated by evaporation and taken up in methylene chloride and water. There is obtained from the organic phase 1-[4-(3-chloropropionylamino)benzoyl]-4-[2-(4-chlorophenyl)-ethyl]piperazine having a melting point of 190°-191°.

EXAMPLE 17

Analogously to Example 16, 1-[4-(4-chlorobutyrylamino)benzoyl]-4-[2-(4-chlorophenyl)ethyl]piperazine having a melting point of 155°-156° is prepared from 2 g of 1-(4-aminobenzoyl)-4-[2-(4-chlorophenyl)ethyl]piperazine and 0.9 g of 4-chlorobutyric acid chloride.

EXAMPLE 18

Analogously to Example 16, 1-[4-(5-chlorovaleroylamino)benzoyl]-4-[2-(4-chlorophenyl)ethyl]piperazine having a melting point of 115°-116° is prepared from 2 g of 1-(4-aminobenzoyl)-4-[2-(4-chlorophenyl)ethyl]piperazine and 0.98 g of 5-chlorovaleric acid chloride.

EXAMPLE 19

0.5 g of 1-[4-(3-chloropropionylamino)benzoyl]-4-[2-(4-chlorophenyl)ethyl]-piperazine and 0.4 g of triethylamine are dissolved in 20 ml of methylene chloride, and the solution is boiled under reflux for 4 hours and then concentrated by evaporation, yielding 1-(4-acryloylaminobenzoyl)-4-[2-(4-chlorophenyl)ethyl]piperazine having a melting point of 163°-165°.

EXAMPLE 20

In a manner analogous to that described in Examples 1 to 19, the following may also be prepared:

(a) 1-[4-(N,N-dimethylaminoacetylamino)benzoyl]-4-[2-(4-chlorophenyl)ethyl]piperazine;

(b) 1-[4-(piperidinoacetylamino)benzoyl]-4-[2-(4-chlorophenyl)ethyl]piperazine.

EXAMPLE 21

5 g of 1-{4-[N-(2-isopropyloxyethyl)-N-chloroacetylamino]benzoyl}-4-[2-(4-chlorophenyl)ethyl]piperazine (Example 3) are dissolved in 50 ml of absolute ethanol, and 1.471 g of sodium thiophenolate are added. The mixture is stirred for one hour at room temperature and a further 1 g of sodium thiophenolate is added. The mixture is stirred for a further 3 hours at RT and then the reaction solution is concentrated by evaporation. The oily residue is extracted with ether and the ethereal phases are washed in succession with water, soda solution and water a concentrated by evaporation, and the light-yellow oil is crystallised from ether and hexane, yielding 1-{4-[N-(2-isopropyloxyethyl)-N-phenylmercaptoacetylamino]benzoyl{-4-[2-(4-chlorophenyl)ethyl]piperazine having a melting point of 47°-49°.

EXAMPLE 22

5 g of 1-{4-[N-(2-isopropyloxyethyl)amino]benzoyl}-4-[2-(4-chlorophenyl)ethyl]piperazine (Example 1) are dissolved in 50 ml of absolute tetrahydrofuran and cooled to 3° with stirring. There are added thereto 1.8 g of Hünig base and then, dropwise, within a period of 5 minutes, a solution of 1.38 g of methoxyacetyl chloride in 5 ml of absolute tetrahydrofuran. The mixture is stirred for 30 minutes at RT and concentrated by evaporation. The residue is taken up in water and ethyl acetate and the organic phase is washed until neutral with sodium hydrogen carbonate solution and water and concentrated by evaporation. The brown oil is chromatographed over silica gel. The mixture is treated with ethereal hydrochloric acid. Recrystallisation from acetone and ether yield 1-{4-[N-(2-isopropyloxyethyl)-N-methoxyacetylamino]benzoyl}-4-[2-(4-chlorophenyl)ethyl]-piperazine hydrochloride having a melting point of 149°-151°.

EXAMPLE 23

3 g of 1-{4-[N-(2-isopropyloxyethyl)amino]benzoyl}-4-[2-(4-chlorophenyl)ethyl]piperazine are dissolved in 40 ml of absolute tetrahydrofuran and cooled to 3° with stirring. There are added thereto 1.08 g of Hünig base and then, dropwise, within a period of 5 minutes, a solution of 0.65 g of acrylic acid chloride in 5 ml of absolute tetrahydrofuran. The mixture is stirred for 30 minutes at RT and concentrated by evaporation. The residue is taken up in water and ethyl acetate and the organic phase is washed until neutral with sodium hydrogen carbonate solution and water and concentrated by evaporation. The brown oil is chromatographed over silica gel. The mixture is treated with ethereal hydrochloric acid. Recrystallisation from acetone and ether yields 1-{4-[N-(2-isopropyloxyethyl)-N-acryloylamino]benzoyl}-4-[2-(4-chlorophenyl)ethyl]-piperazine hydrochloride having a melting point of 132°-134°.

EXAMPLE 24

In a manner analogous to that described in Example 23, 1-{4-[N-(2-isopropyloxyethyl)-N-acetylamino]benzoyl}-4-[2-(4-chlorophenyl)ethyl]piperazine hydrochloride having a melting point of 142°-144° is obtained from 3 g of 1-{4-[N-(2-isopropyloxyethyl)amino]benzoyl}-4-[2-(4-chlorophenyl)ethyl]piperazine by reaction with acetyl chloride.

EXAMPLE 25

In a manner analogous to that described in Example 23, 1-{4-[N-(2-isopropyloxyethyl)-N-methoxycarbonylcarbonylamino]benzoyl}-4-[2-(4-chlorophenyl)ethyl]-piperazine hydrochloride having a melting point of 152°-154° is obtained from 3 g of 1-{4-[N-(2-isopropyloxyethyl)amino]benzoyl}-4-[2-(4-chlorophenyl)ethyl]piperazine by reaction with oxalic acid monomethyl ester chloride.

EXAMPLE 25a

Analogously to Example 23, 1-{4-[N-(2-isopropyloxyethyl)-N-(3-methoxycarbonylprop-2-en(Z)-1-on-yl)amino]benzoyl}-4-[2-(4-chlorophenyl)ethyl]piperazine is obtained by reaction of 1-{4-[N-(2-isopropyloxyethyl)amino]benzoyl}-4-[2-(4-chlorophenyl)ethyl]piperazine with maleic acid methyl ester chloride.

EXAMPLE 25b

Analogously to Example 23, 1-{4-[N-(2-isopropyloxyethyl)-N-(3-methoxycarbonylprop-2-en(E)-1-on-yl)amino]benzoyl}-4-[2-(4-chlorophenyl)ethyl]piperazine is obtained by reaction of 1-{4-[N-(2-isopropyloxyethyl)amino]benzoyl}-4-[2-(4-chlorophenyl)ethyl]piperazine with fumaric acid methyl ester chloride.

EXAMPLE 25c

In a manner analogous to that described in Example 23, 1-{4-[N-(2-isopropyloxyethyl)-N-(3-ethoxycarbonylprop-2-en(Z)-1-on-yl)amino]benzoyl}-4-[2-(4-chlorophenyl)ethyl]piperazine is obtained from 1-{4-[N-(2-isopropyloxyethyl)amino]benzoyl}-4-[2-(4-chlorophenyl)ethyl]piperazine and maleic acid ethyl ester chloride. The hydrochloride thereof melts at 181°-183°.

EXAMPLE 25d

In a manner analogous to that described in Example 23, 1-{4-[N-(2-isopropyloxyethyl)-N-(3-ethoxycarbonylprop-2-en(E)-1-on-yl)amino]benzoyl}-4-[2-(4-chlorophenyl)ethyl]piperazine hydrochloride having a melting point of 180°-182° is obtained from 1-{4-[N-(2-isopropyloxyethyl)amino]benzoyl}-4-[2-(4-chlorophenyl)ethyl]piperazine and fumaric acid ethyl ester chloride.

EXAMPLE 26

2.18 g of 4-chlorobenzylpiperazine are dissolved in 40 ml of absolute tetrahydrofuran. With stirring, 1.73 g of Hünig base and 2.64 g of 4-chloroacetylaminobenzoic acid chloride are added thereto in succession. The internal temperature rises to approximately 38°. After 30 minutes, the solution is concentrated by evaporation. The oily residue is digested with water, yielding 1-[4-(N-chloroacetylamino)benzoyl]-4-(4-chlorobenzyl)piperazine having a melting point of 205°-207°.

EXAMPLE 27

In a manner analogous to that described in Example 26, 1-[4-(N-chloroacetylamino)benzoyl]-4-[3-phenylprop-2-enyl]piperazine having a melting point of 141°-144° is obtained from 2.03 g of 1-cinnamylpiperazine [=1-(3-phenylprop-2-enyl)piperazine] and 2.21 g of 4-chloroacetylaminobenzoic acid chloride.

EXAMPLE 28

In a manner analogous to that described in Example 26, 1-[4-(N-chloroacetylamino)benzoyl]-4-[3-(4-chlorophenyl)propyl]piperazine having a melting point of 158°-161° is obtained from 1.54 g of 1-[3-(4-chlorophenyl)propyl]piperazine and 1.24 g of 4-chloroacetylaminobenzoic acid chloride.

EXAMPLE 29

In a manner analogous to that described in Example 22, 1-[2-(N-chloroacetylamino)benzoyl]-4-[2-(4-chlorophenyl)ethyl]piperazine having a melting point of 108°-109° is obtained from 2 g of 1-(2-aminobenzoyl)-4-[2-(4-chlorophenyl)ethyl]-piperazine by reaction with chloroacetyl chloride.

The starting material is prepared as follows: 10 g of isatic acid anhydride are suspended in 100 ml of dioxane. The suspension is heated to 60° IT, and within a period of 10 minutes 13.74 g of 1-[2-(4-chlorophenyl)ethyl]piperazine in 20 ml of dioxane are added dropwise. The mixture is boiled under reflux for 30 minutes and then concentrated by evaporation. The residue is dissolved in ether and washed with soda solution (1%). The ether solution is concentrated by evaporation and the yellow oil is recrystallised from hexane, yielding 1-(2-aminobenzoyl)-4-[2-(4-chlorophenyl)ethyl]piperazine having a melting point of 78°-80°.

EXAMPLE 30

In a manner analogous to that described in Example 26, 1-[4-(N-chloroacetylamino)benzoyl]-4-[4-(4-chlorophenyl)butyl]piperazine having a melting point of 158°-160° is obtained from 2 g of 1-[4-(4-chlorophenyl)butyl]piperazine (see U.S. Pat. No. 4,725,597) and 1.93 g of 4-chloroacetylaminobenzoic acid chloride.

EXAMPLE 31

In a manner analogous to that described in Example 26, 1-[3-(N-chloroacetylamino)benzoyl]-4-[2-(4-chlorophenyl)ethyl]piperazine having a melting point of 125°-126° is obtained from 2.5 g of 1-[2-(4-chlorophenyl)ethyl]piperazine and 2.72 g of 3-chloroacetylaminobenzoic acid chloride (see U.S. Pat. No. 4,093,739).

EXAMPLE 32

In a manner analogous to that described in Example 26, 1-[4-(N-chloroacetylamino)benzoyl]-4-(2-chlorophenyl)piperazine having a melting point of 177°-179° is obtained from 2.33 g of 1-(2-chlorophenyl)piperazine and 2.44 g of 4-chloroacetylaminobenzoic acid chloride.

EXAMPLE 33

0.42 g of 50% sodium hydride dispersion is introduced into 25 ml of absolute dimethylformamide. A solution of 1-[4-N-dimethylcarbamoylamino)benzoyl]-4-[2-(4-chlorophenyl)ethyl]piperazine in 30 ml of absolute dimethylformamide is added dropwise thereto at RT. After approximately 15 minutes, the evolution of gas begins. After 5 minutes at 60° IT, it has ceased. A solution of 2-isopropyloxyethyl bromide in 5 ml of absolute dimethylformamide is added at 30°. The mixture is stirred for one hour at RT and for a further 4 hours at 60°. The mixture is concentrated by evaporation and chromatographed over silica gel with alcoholic hydrochloric acid, yielding 1-{4-[N-(2-isopropyloxyethyl)-N-(N′,N′-dimethylcarbamoyl)amino)benzoyl}-4-[2-(4-chlorophenyl)-ethyl]piperazine hydrochloride having a melting point of 179°-181°.

EXAMPLE 34

In a manner analogous to that described in Example 26, 1-[4-(N-chloroacetylamino)benzoyl]-4-(4-chlorophenyl)piperazine having a melting point of 218°-221° is obtained from 2 g of 1-(4-chlorophenyl)piperazine and 2.36 g of 4-chloroacetylaminobenzoic acid chloride.

EXAMPLE 35

In a manner analogous to that described in Example 26, 1-[4-(N-chloroacetylamino)benzoyl]-4-(3-chlorophenyl)piperazine having a melting point of 174°-175° is obtained from 5.02 g of 1-(3-chlorophenyl)piperazine and 6.51 g of 4-chloroacetylaminobenzoic acid chloride.

EXAMPLE 36

In a manner analogous to that described in Example 26, 1-[4-(N-chloroacetylamino)phenylacetyl]-4-[2-(4-chlorophenyl)ethyl]piperazine having a melting point of 163°-165° is obtained from 1.66 g of 1-[(4-chlorophenyl)ethyl]piperazine and 2 g of 4-chloroacetylaminophenylacetic acid chloride [see J. Amer. Chem. Soc. 41 (1919) 469].

EXAMPLE 37

3.4 g of 1-(4-aminobenzoyl)-4-[2-(4-chlorophenyl)-piperazine are dissolved in 100 ml of absolute dichloromethane. There are added thereto 1.2 g of triethylamine and, dropwise, 1.3 g of dimethylcarbamoyl chloride in 5 ml of absolute dichloromethane. After 20 hours at RT, 0.12 g of 4-dimethylaminopyridine is added, and the mixture is stirred for a further 4 hours at RT. The organic phase is washed with water and concentrated by evaporation. The highly viscous oil can be crystallised in the form of the hydrochloride. In this manner, 1-[4-(N-dimethylcarbamoylamino)benzoyl]-4-[2-(4-chlorophenyl)ethyl]piperazine hydrochloride having a melting point of 245°-247° is obtained.

EXAMPLE 38

In a manner analogous to that described in Example 26, 1-[4-(N-chloroacetylamino)phenylacetyl]-4-(4-chlorophenyl)piperazine having a melting point of 195°-197° is obtained from 1.45 g of 1-(4-chlorophenyl)-piperazine and 1.99 g of 4-chloroacetylaminophenylacetic acid chloride.

EXAMPLE 39

1.55 g of 1-{4-[N-(2-isopropyloxyethyl)-N-phenylmercaptoacetylamino]benzoyl}-4-[2-(4-chlorophenyl)ethyl]piperazine (Example 21) are dissolved in 50 ml of dichloromethane and stirred. 0.56 g of m-chloroperbenzoic acid (90%) is added thereto, whereupon the IT rises to 26°. After 30 minutes, a further 0.1 g of m-chloroperbenzoic acid (90%) is added. After a further 15 minutes, the solution is concentrated by evaporation. The residue is taken up in water and ethyl acetate and the organic phase is washed until neutral with sodium hydrogen carbonate solution and water and concentrated by evaporation. The residue is digested with ether, yielding 1-{4-[N-(2-isopropyloxyethyl)-N-phenylsulfonylacetylamino]benzoyl}-4-[2-(4-chlorophenyl)ethyl]piperazine having a melting point of 115°-116°.

EXAMPLE 40

In a manner analogous to that described in Example 23, 1-{4-[N-(2-isopropyloxyethyl)-N-methoxycarbonylacetylamino]benzoyl}-4-[2-(4-chlorophenyl)ethyl]piperazine hydrochloride having a melting point of 77°-79° is obtained from 1 g of 1-{4-[N-(2-isopropyloxyethyl)amino]benzoyl}-4-[2-(4-chlorophenyl)ethyl]piperazine (Example 1) by reaction with malonic acid monomethyl ester chloride.

EXAMPLE 41

In a manner analogous to that described in Example 23, 1-{4-[N-(2-isopropyloxyethyl)-N-acetoxyacetylamino]benzoyl}-4-[2-(4-chlorophenyl)ethyl]piperazine hydrochloride having a melting point of 130°–132° is obtained from 5 g of 1-{4-[N-(2-isopropyloxyethyl)amino]benzoyl}-4-[2-(4-chlorophenyl)ethyl]piperazine (Example 21) by reaction with acetoxyacetic acid chloride.

EXAMPLE 42

1.2 g of 1-{4-[N-(2-isopropyloxyethyl)-N-acetoxyacetylamino]benzoyl}-4-[2-(4-chlorophenyl)ethyl]piperazine (Example 41) are dissolved in 20 ml of ethanol. 1.5 ml of 2N sodium hydroxide solution in 5 ml of water are added thereto, and the mixture is stirred at RT for one hour. After concentration by evaporation, the residue is dissolved in ethyl acetate and washed with water. Concentration by evaporation and treatment with ethereal hydrochloric acid yield 1-{4-[N-(2-isopropyloxyethyl)-N-hydroxyacetylamino]benzoyl}-4-[2-(4-chlorophenyl)ethyl]piperazine hydrochloride having a melting point of 99°–101°.

EXAMPLE 43

1.2 g of 1-{4-[N-(2-isopropyloxyethyl)amino]benzoyl}-4-[2-(4-chlorophenyl)ethyl]piperazine are dissolved in 15 ml of toluene, and 1.1 g of potash are added. The mixture is stirred for 10 minutes at RT and then 1.9 g of chloroformic acid benzyl ester in 4 ml of toluene are added dropwise thereto. The mixture is stirred overnight at RT and concentrated by evaporation, the residue is partitioned between dichloromethane and water, and the mixture is concentrated by evaporation and chromatographed over silica gel (eluant: dichloromethane/acetone 9:1). Treatment with alcoholic hydrochloric acid yields 1-{4-[N-(2-isopropyloxyethyl)benzyloxycarbonylamino]benzoyl}-4-[2-(4-chlorophenyl)ethyl]piperazine hydrochloride having a melting point of 135°–137°.

EXAMPLE 44

0.85 g of 1-{4-[N-(3-ethoxypropyl)amino]benzoyl}-4-[2-(4-chlorophenyl)ethyl]piperazine are dissolved in 20 ml of absolute tetrahydrofuran, and there are added in succession 0.33 g of Hünig base and 1.34 ml of chloroformic acid benzyl ester in toluene.

After stirring for 30 minutes at RT, the mixture is concentrated by evaporation and extracted by shaking with ethyl acetate, hydrochloric acid is added and the mixture is concentrated by evaporation again. Recrystallisation from hexane/ether yields 1-{4-[N-3-ethoxypropyl)benzyloxycarbonylamino]benzoyl}-4-[2-(4-chlorophenyl)ethyl]piperazine hydrochloride having a melting point of 113°–115°.

EXAMPLE 45

200 g of 1-[N-(tert-butyloxycarbonylamino)benzoyl]-4[2-(4-chlorophenyl)ethyl]piperazine are dissolved in 700 ml of N,N-dimethylformamide, and 34 g of powdered KOH are added. The mixture is stirred for 30 minutes at RT; then a solution of 136 g of O-(2-isopropyloxyethyl) tosylate in 150 ml of N,N-dimethylformamide is added dropwise within a period of 15 minutes. The mixture is stirred for 30 minutes at RT and for 4 hours at 45°–50°, concentrated by evaporation, extracted with ether, washed with water and concentrated by evaporation. Treatment with alcoholic hydrochloric acid yields 1-{4-[N-(2-isopropoxyethyl)-tert-butyloxycarbonylamino]benzoyl}-4-[2-(4-chlorophenyl)ethyl]piperazine hydrochloride having a melting point of 182°–184°.

EXAMPLE 46

2 g of 4-(ethylsulfinylacetylamino)benzoic acid are suspended with 1.5 g of N,N-carbonyldiimidazole in 30 ml of absolute dimethylformamide and heated for 20 minutes at 80° ET. A clear solution is obtained, to which 1.75 g of 1-[2-(4-chlorophenyl)ethyl]piperazine are added at 80°. After 30 minutes at 80°, the solution is concentrated by evaporation. The residue is dissolved in dichloromethane and washed with water, chromatographed over silica gel and crystallized from ethanol, yielding 1-[4-(N-ethylsulfinylacetylamino)benzoyl]-4-[2-(4-chlorophenyl)ethyl]piperazine having a melting point of 163°–164°.

The starting material is prepared as follows: 9.2 g of 4-(ethylmercaptoacetylamino)benzoic acid are dissolved in 200 ml of absolute tetrahydrofuran. A solution of 3-chloroperbenzoic acid in 40 ml of absolute tetrahydrofuran is added dropwise at 35°. The mixture is stirred overnight at RT. The suspension is filtered off with suction and the crystalline product is recrystallised from ethanol. The 4-(ethylsulfinylacetylamino)benzoic acid melts at 203°–205°.

EXAMPLE 47

1.4 g of 1-[4-(N-ethylsulfinylacetylamino)benzoyl]-4-[2-(4-chlorophenyl)ethyl]piperazine (Example 46) are dissolved in 50 ml of dimethylformamide, and a solution of 3-chloroperbenzoic acid (85%) in 30 ml of tetrahydrofuran is added dropwise at RT. The clear solution is stirred overnight at RT. The mixture is concentrated by evaporation, the residue is dissolved in water and the solution is rendered neutral, extracted with dichloromethane, chromatographed over silica gel and crystallised from ether/petroleum ether/alcohol, yielding 1-[4-(N-ethylsulfonylacetylamino)benzoyl]-4-[2-(4-chlorophenyl)ethyl]piperazine having a melting point of 135°–136°.

EXAMPLE 48

1.15 g of N-(2-isopropyloxyethyl)isatic acid anhydride (=N-(2-isopropyloxyethyl)-dihydro-2,4-dioxo-3,1-benzoxazine) are dissolved in 20 ml of dioxane, and 0.942 g of 1-[2-(4-chlorophenyl)ethyl]piperazine is added thereto. The mixture is stirred at 50° IT, whereupon $CO_2$ is immediately liberated. After one hour, the reaction solution is concentrated by evaporation, the residue is taken up in ethyl acetate, and the organic phase is washed with water until neutral. The mixture is concentrated by evaporation and chromatographed over silica gel. Treatment with ethereal hydrochloric acid yields 1-{2-[N-(2-isopropyloxyethyl)amino]benzoyl}-4-[2-(4-chlorophenyl)ethyl]piperazine hydrochloride having a melting point of 237°–240°.

The starting material is prepared as follows: 3 g of isatic acid anhydride are dissolved in 50 ml of distilled hexametapol(=hexamethylphosphoric acid triamide). The solution is cooled to 5°, and 0.96 g of 55% NaH (freed of oil with hexane) is added. The mixture is stirred for 30 minutes at RT and then 5.67 g of O-(2-isopropyloxyethyl) tosylate are added. The mixture is stirred for 30 minutes at RT and for one hour at 50°. The mixture is left to stand overnight and is poured onto ice, and the organic layer is separated off and washed with water. The mixture is concentrated by evaporation, and the residue is digested with ether and filtered off with suction, yielding N-(2-isopropyloxyethyl)isatic acid anhydride, m.p. 107°–108°.

EXAMPLE 49

0.82 g of 1-{2-[N-(2-isopropyloxyethyl)amino]benzoyl}-4-[2-(4-chlorophenyl)ethyl]piperazine (Example 48) are introduced into 30 ml of absolute tetrahydrofuran. 0.295 g of Hünig base is added thereto with external cooling, followed by a solution of 0.236 g of chloroacetyl chloride in 2 ml of absolute tetrahydrofuran. After stirring for 30 minutes at RT, the reaction is complete. The mixture is concentrated by evaporation and the residue is extracted with ethyl acetate, washed with water and concentrated by evaporation again. Treatment with ethereal hydrochloric acid yields 1-{2-[N-(2-isopropyloxyethyl)-N-chloroacetylamino]benzoyl}-4-[2-(4-chlorophenyl)ethyl]-piperazine hydrochloride having a melting point of 112°–113°.

EXAMPLE 50

In a manner analogous to that described in Example 26, there is obtained from 7.72 g of 1-[2-(4-chlorophenyl)ethyl]piperazine and 8 g of 4-(N-chloroacetyl-N-methylamino)benzoic acid chloride, 1-[4-(N-chloroacetyl-N-methylamino)benzoyl]-4-[2-(4-chlorophenyl)ethyl]piperazine, which, after purification by chromatography over silica gel (eluant: CH$_2$Cl$_2$/acetone), has a melting point of 113°–115°.

The starting material is prepared as follows: There are added to 30 g of 4-(N-methylamino)benzoic acid in 500 ml of dichloromethane 30.7 g of Hünig base and, at 5°, 24.6 g of chloroacetyl chloride in 50 ml of dichloromethane. After stirring for 2 hours at RT, the suspension is concentrated by evaporation, and the residue is digested with water, filtered with suction and washed with 1N hydrochloric acid. The mixture is digested with ether and filtered with suction, yielding 4-(N-chloroacetyl-N-methylamino)benzoic acid having a melting point (186°) of 195°–197°. 10 g thereof are boiled under reflux for 2 hours in 150 ml methylene chloride with 5 drops of pyridine with 15 ml of thionyl chloride, concentrated by evaporation and recrystallised from hexane. The resulting 4-(N-chloroacetyl-N-methylamino)benzoic acid chloride melts at 61°–63°.

EXAMPLE 51

0.9 g of glycine ethyl ester hydrochloride is dissolved in 20 ml of ethanol, and 0.87 g of Hünig base and 0.5 g of 1-{4-[N-(2-isopropyloxyethyl)-N-chloroacetylamino]benzoyl}-4-[2-(4-chlorophenyl)ethyl]piperazine (Example 3) are added. The mixture is boiled under reflux for 24 hours. The mixture is concentrated by evaporation, and the residue is dissolved in ethyl acetate and washed with water until neutral. Concentration by evaporation and treatment with ethereal hydrochloric acid yield 1-{4-[N-(2-isopropyloxyethyl)-N-(N'-ethoxycarbonylmethylamino)acetylamino]benzoyl}-4-[2-(4-chlorophenyl)ethyl]piperazine hydrochloride having a melting point of 124°–126°.

EXAMPLE 52

65 ml of trifluoroacetic acid are introduced into 100 ml of dichloromethane. A solution of 7.2 g of 1-{3-[N-(2-isopropyloxyethyl)-N-tert-butoxycarbonylamino]-benzoyl}-4-[2-(4-chlorophenyl)ethyl]piperazine is added thereto within a period of 5 minutes. After 2 hours at RT, the reaction solution is concentrated by evaporation and the residue is neutralised with sodium hydroxide solution and extracted with ether. Concentration by evaporation and treatment with ethereal hydrochloric acid yield 1-[3-(2-isopropyloxyethylamino)-benzoyl]-4-[2-(4-chlorophenyl)ethyl]piperazine hydrochloride having a melting point of 157°–159°.

Starting materials: (a) 3-acetylaminobenzoic acid is converted by means of thionyl chloride into the acid chloride [m.p. 101°–102°], and the latter is then condensed with 1-[2-(4-chlorophenyl)ethyl]piperazine, yielding 1-(3-acetylaminobenzoyl)-4-[2-(4-chlorophenyl)ethyl]piperazine in the form of a foam. The latter is reacted with (BOC)$_2$O to form 1-{3-[(N-acetyl-N-tert-butyloxycarbonyl)amino]benzoyl}-4-[2-(4-chlorophenyl)ethyl]piperazine having a melting point of 113°–114°. The subsequent cleavage with dimethylaminoethylamine results in a foam, which corresponds to 1-[3-(N-tert-butyloxycarbonylamino)benzoyl]-4-[2-(4-chlorophenyl)ethyl]piperazine.

(b) 6 g of 1-[3-(N-tert-butyloxycarbonylamino)benzoyl]-4-[2-(4-chlorophenyl)ethyl]piperazine and 4.18 g of 2-isopropyloxyethyl p-toluenesulfonate are reacted in DMSO in the presence of 1.01 g of finely powdered KOH. The oily 1-{3-[N-(2-isopropyloxyethyl)-N-tert-butoxycarbonylamino]benzoyl}-4-[2-(4-chlorophenyl)ethyl]piperazine so obtained is reacted further directly.

EXAMPLE 53

2.77 g of 1-[3-(2-isopropyloxyethylamino)benzoyl]-4-[2-(4-chlorophenyl)ethyl]piperazine are dissolved in 50 ml of absolute tetrahydrofuran and stirred at RT with 1.07 g of Hünig base and 0.794 g of chloroacetyl chloride in 5 ml of absolute tetrahydrofuran. After approximately 15 minutes, the thin suspension is concentrated by evaporation, dissolved in ethyl acetate and washed with water until neutral. Concentration by evaporation, chromatography of the residue over silica gel (eluant: ethyl acetate) and treatment with ethereal hydrochloric acid yield 1-{3-[N-(2-isopropyloxyethyl)-N-chloroacetylamino]benzoyl}-4-[2-(4-chlorophenyl)ethyl]piperazine hydrochloride having a melting point of 115°–117°.

EXAMPLE 54a

Analogously to Example 22, 1-[4-(2-dimethylaminoethylamino)benzoyl]-4-[2-(4-chlorophenyl)ethyl]piperazine (Example 54b) is reacted with chloroacetyl chloride, yielding 1-{4-[N-(2-dimethylaminoethyl)-N-chloroacetylamino]benzoyl}-4-[2(4-chlorophenyl)ethyl]piperazine. The hydrochloride thereof melts at 215°–216° (decomposition).

EXAMPLE 54b 1.9 g of 1-{4-[N-(2-dimethylaminoethyl)-N-benzyloxycarbonylamino]-benzoyl}-4-[2-(4-chlorophenyl)ethyl]piperazine are hydrogenated in 30 ml of methanol in the presence of 0.4 g of palladium-on-carbon. The mixture is filtered off with suction, concentrated by evaporation, rendered alkaline with 2N NaOH and extracted with ether. The mixture is concentrated by evaporation and recrystallised from ether. The 1-[4-(2-dimethylaminoethylamino)benzoyl]-4-[2-(4-chlorophenyl)ethyl]piperazine melts at 74°–78°. With alcoholic hydrochloric acid, 1-[4-(2-dimethylaminoethylamino)benzoyl]-4-[2-(4-chlorophenyl)ethyl]piperazine hydrochloride having a melting point >275° is obtained.

The starting material is prepared as follows: 0.5 g of 50% NaH dispersion is suspended in 15 ml of absolute N,N-dimethylformamide. A solution of 4.7 g of 1-[4-(N-benzyloxycarbonylamino)benzoyl]-4-[2-(4-chlorophenyl)ethyl]piperazine (see European Patent Application No. 489 690, Example 28) in 30 ml of N,N-dimethylformamide is added dropwise thereto. After 30 minutes, 1.18 g of 1-chloro-2-dimethylaminoethane in 1 ml of N,N-dimethylformamide are added. The mixture is stirred overnight at RT. The mixture is concentrated by evaporation, water is added to the residue, and the mixture is extracted by shaking with ethyl acetate, concentrated by evaporation and chromatographed over silica gel (eluant: dichloromethane/acetone/methanol 70:30:8). The viscous oil corresponds to 1-{4-[N-(2-dimethylaminoethyl)-N-benzyloxycarbonylamino]benzoyl}-4-[2-(4-chlorophenyl)ethyl]piperazine and is reacted further directly.

EXAMPLE 55

0.8 g of 1-(2-phenylethyl)piperazine are dissolved in 15 ml of dichloromethane, and there are added in succession 0.56 g of Hünig base and 1.5 g of 4-(N-2-isopropyloxyethyl-N-chloroacetylamino)benzoyl chloride in 5 ml of dichloromethane. The mixture is stirred overnight, concentrated by evaporation, and partitioned between dichloromethane and water, and the organic phase is concentrated by evaporation and chromatographed over silica gel (eluant: dichloromethane/acetone 50:8 and 50:10). Treatment with alcoholic hydrochloric acid yields 1-{4-[N-(2-isopropyloxyethyl)-N-chloroacetylamino]benzoyl}-4-(2-phenylethyl)piperazine hydrochloride having a melting point of 170°–171°.

The starting material is prepared as follows: (a) 22.4 g of 4-aminobenzoic acid ethyl ester are left to stand overnight at RT in 220 ml of pyridine and 220 ml of acetic anhydride. The mixture is concentrated by evaporation, the residue is taken up in water and dichloromethane, and the organic phase is washed until neutral, concentrated and diluted with ether. The 4-acetylaminobenzoic acid ethyl ester which crystallises out is filtered off with suction; m.p. 110°–111°.

(b) 8.3 g thereof are dissolved in 100 ml of acetonitrile, and 0.5 g of 4-dimethylaminopyridine is added. Within a period of 5 minutes, 10.5 g of (BOC)₂O in 50 ml of acetonitrile are added dropwise thereto. The mixture is left to stand overnight at RT, then a further 1.5 g of (BOC)₂O are added and the mixture is left to stand for a further 6 hours. 4-(N-Acetyl-N-tert-butyloxycarbonylamino)benzoic acid ethyl ester is obtained in solution. 8 g of 2-diethylaminoethylamine are added to that solution, and the mixture is left to stand overnight. The mixture is concentrated by evaporation, and the residue is taken up in ethyl acetate and washed with water, concentrated, filtered off with suction and washed with petroleum ether/ethyl acetate, yielding 4-tert-butyloxycarbonylaminobenzoic acid ethyl ester, m.p. 149°–150°.

(c) 2.6 g thereof are dissolved in 15 ml of N,N-dimethylformamide, and 0.7 g of powdered KOH is added thereto. The mixture is stirred for 15 minutes at RT, then 3 g of O-(2-isopropyloxyethyl) tosylate in 5 ml of N,N-dimethylformamide are quickly added dropwise, and then the mixture is kept for 5.5 hours at 45°–50° IT and overnight at RT. The mixture is poured onto ice, acidified with 2N HCl and extracted with ether, concentrated by evaporation and chromatographed over silica gel (eluant: dichloromethane), yielding 4-[N-tert-butyloxycarbonyl-N-(2-isopropyloxyethyl)amino]benzoic acid ethyl ester in the form of an oil. It is used further directly.

(d) 7.7 g thereof are dissolved in 100 ml of dichloromethane; 60 ml of trifluoroacetic acid are added, and the mixture is stirred for 20 hours at RT. It is concentrated by evaporation, water is added to the residue, and the mixture is rendered alkaline with ammonia and extracted with dichloromethane. The mixture is concentrated by evaporation, and the crude 4-[N-(2-isopropyloxyethyl)]benzoic acid ethyl ester is hydrolysed in 50 ml of ethanol with 21.6 ml of 2N NaOH overnight at RT and then for a further 4 hours at 50°–55°. 21.6 ml of 2N HCl are added thereto. The precipitate is filtered off with suction, yielding 4-[N-(2-isopropyloxyethyl)amino]benzoic acid having a melting point of 116°–118°.

(e) To 0.22 g thereof in 10 ml of dichloromethane there is added a solution of 0.17 g of chloroacetyl chloride in 3 ml of dichloromethane. The mixture is left to stand overnight at RT, and concentrated by evaporation, the residue is taken up in ether, washed with water, concentrated to approximately 15 ml, and petroleum ether is added. The crystallisate is filtered off with suction, yielding 4-[N-(2-isopropyloxyethyl)-N-chloroacetylamino]benzoic acid having a melting point of 129°–130°.

EXAMPLE 56

Analogously to Example 55, 1.5 g of 4-[N-(2-isopropyloxyethyl)-N-chloroacetylamino]benzoyl chloride are reacted with 1.07 g of [2-(4-bromophenyl)ethyl]-piperazine, yielding 1-{4-[N-(2-isopropyloxyethyl)-N-chloroacetylamino]benzoyl}-4-[2-(4-bromophenyl)ethyl]piperazine having a melting point of 92°–93°.

EXAMPLE 57

Analogously to Example 55, 1.5 g of 4-[N-(2-isopropyloxyethyl)-N-chloroacetylamino]benzoyl chloride are reacted with 0.9 g of [2-(4-fluorophenyl)ethyl]-piperazine, yielding 1-{4-[N-(2-isopropyloxyethyl)-N-chloroacetylamino]benzoyl}-4-[2-(4-fluorophenyl)ethyl]piperazine. The hydrochloride thereof melts at 166°–167°.

EXAMPLE 58

Analogously to Example 55, 1.5 g of 4-[N-(2-isopropyloxyethyl)-N-chloroacetylamino]benzoyl chloride are reacted with 0.95 g of [2-(4-methylmercaptophenyl)ethyl]piperazine, yielding 1-{4-[N-(2-isopropyloxyethyl)-N-chloroacetylamino]benzoyl}-4-[2-(4-methylmercaptophenyl)ethyl]piperazine. The hydrochloride thereof melts at 115°–116°.

EXAMPLE 59

Analogously to Example 55, 1.5 g of 4-[N-(2-isopropyloxyethyl)-N-chloroacetylamino]benzoyl chloride are reacted with 0.88 g of [2-(4-methoxyphenyl)ethyl]piperazine, yielding 1-{4-[N-(2-isopropyloxyethyl)-N-chloroacetylamino]benzoyl}-4-[2-(4-methoxyphenyl)ethyl]piperazine. The hydrochloride thereof melts at 139°–140°.

EXAMPLE 59a

Analogously to Example 55, 1.5 g of 4-[N-(2-isopropyloxyethyl)-N-chloroacetylamino]benzoyl chloride are reacted with 0.8 g of [2-(4-chlorophenyl)ethyl]-piperazine, yielding 1-{4-[N-(2-isopropyloxyethyl)-N-chloroacetylamino]benzoyl}-4-[2-(4chlorophenyl)ethyl]piperazine having a melting point of 82°–83°.

EXAMPLE 59b

Analogously to Example 55, 1.5 g of 4-[N-(2-isopropyloxyethyl)-N-chloroacetylamino]benzoyl chloride are reacted with 0.76 g of 2-methylbenzylpiperazine, yielding 1-{4-[N-(2-isopropyloxyethyl)-N-chloroacetylamino]benzoyl}-4-(2-methylbenzyl)piperazine. The hydrochloride thereof melts at 142°–143°.

EXAMPLE 60

Analogously to Example 55, 1.5 g of 4-[N-(2-isopropyloxyethyl)-N-chloroacetylamino]benzoyl chloride are reacted with 0.81 g of cinnamylpiperazine (Example 27), yielding 1-{4-[N-(2-isopropyloxyethyl)-N-chloroacetylamino]benzoyl}-4-[3-phenylprop-2-enyl]-piperazine. The hydrochloride thereof melts at 188°–190°.

EXAMPLE 61

In a manner analogous to that described in Example 22, 1-{4-[N-(2-isopropyloxyethyl)amino]benzoyl}-4-[2-(4-chlorophenyl)ethyl]piperazine (Example 1) and N,N-dimethylglycine chloride are reacted, yielding 1-{4-[N-(2-isopropyloxyethyl)-N,N-dimethylaminoacetylamino]benzoyl}-4-[2-(4-chlorophenyl)ethyl]piperazine. The difumarate thereof melts at 187°–188°.

EXAMPLE 62

Analogously to Example 51, 1-{4-[N-(2-isopropyloxyethyl)-N-chloroacetylamino]benzoyl}-4-[2-(4-chlorophenyl)ethyl]piperazine (Example 3) and piperidine are reacted, yielding 1-{4-[N-(2-isopropyloxyethyl)-N-piperidinoacetylamino]benzoyl}-4-[2-(4-chlorophenyl)ethyl]piperazine. The difumarate thereof melts at 179°–180°.

EXAMPLE 63

1.02 g of 1-(2-chloro-4-aminobenzoyl)-4-[2-(4-chlorophenyl)ethyl]piperazine (see European Patent Application No. 489 690, Example 7) in 50 ml of absolute tetrahydrofuran are acylated with 0.33 g of chloroacetyl chloride analogously to Example 22, yielding 1-[(2-chloro-4-chloroacetylamino)benzoyl]-4-[2-(4-chlorophenyl)ethyl]piperazine hydrochloride having a melting point of 290°–293°.

EXAMPLE 64

Analogously to Example 63, 1-(4-fluoro-3-aminobenzoyl)-4-[2-(4-chlorophenyl)ethyl]piperazine is reacted with chloroacetyl chloride, yielding 1-[(4-fluoro-3-chloroacetylamino)benzoyl]-4-[2-(4-chlorophenyl)ethyl]piperazine.

EXAMPLE 65

Analogously to Example 63, 1-(2-chloro-3-aminobenzoyl)-4-[2-(4-chlorophenyl)ethyl]piperazine is reacted with chloroacetyl chloride, yielding 1-[(2-chloro-3-chloroacetylamino)benzoyl]-4-[2-(4-chlorophenyl)ethyl]piperazine having a melting point of 156°–157°.

EXAMPLE 66

1.75 g of Hünig base and 2.59 g of 1-[2-(4-chlorophenyl)ethyl]piperazine in 40 ml of tetrahydrofuran are added dropwise at 5° to 3 g of 4-chloro-3-chloroacetylaminobenzoic acid chloride (prepared from the corresponding acid with thionyl chloride, m.p. 139°–140°) in 12 ml of absolute tetrahydrofuran. After stirring for 30 minutes at RT, the mixture is concentrated by evaporation. The residue is taken up in ether, washed with water and concentrated, and the precipitate is filtered off with suction, yielding 1-[(4-chloro-3-chloroacetylamino)benzoyl]-4-[2-(4-chlorophenyl)ethyl]piperazine having a melting point of 64°–65°.

EXAMPLE 67

Analogously to Example 66, 3-methoxy-4-chloroacetylaminobenzoic acid chloride is reacted with 1-[2-(4-chlorophenyl)ethyl]piperazine, yielding 1-[(3-methoxy-4-chloroacetylamino)benzoyl]-4-[2-(4-chlorophenyl)ethyl]piperazine.

EXAMPLE 68

Analogously to Example 66, 3-methyl-4-chloroacetylaminobenzoic acid chloride (m.p. 105°–106°) is reacted with 1-[2-(4-chlorophenyl)ethyl]piperazine, yielding 1-[(3-methyl-4-chloroacetylamino)benzoyl]-4-[2-(4-chlorophenyl)ethyl]piperazine having a melting point of 143°–145°.

EXAMPLE 69

Analogously to Example 29, the following compounds are synthesised from the correspondingly substituted isatic acid anhydrides:

(a) 1-[(3-chloro-2-chloroacetylamino)benzoyl]-4-[2-(4-chlorophenyl)ethyl]piperazine (b) 1-[(4-chloro-2-chloroacetylamino)benzoyl]-4-[2-(4-chlorophenyl)ethyl]piperazine (c) 1-[(5-chloro-2-chloroacetylamino)benzoyl]-4-[2-(4-chlorophenyl)ethyl]piperazine, m.p. 140°–141°

(d) 1-[(3,5-dichloro-2-chloroacetylamino)benzoyl]-4-[2-(4-chlorophenyl)ethyl]piperazine.

EXAMPLE 70

Analogously to Examples 2 and 3, the following compounds are synthesised:

(a) 1-{4-[N-(2-methoxyethyl)-N-chloroacetylamino]benzoyl}-4-[2-(4-chlorophenyl)ethyl]piperazine (b) 1-{4-[N-(2-(2-methoxyethoxy)ethyl)-N-chloroacetylamino]benzoyl}-4-[2-(4-chlorophenyl)ethyl]piperazine (c) 1-{4-[N-(2-n-butyloxyethyl)-N-chloroacetylamino]benzoyl}-4-[2-(4-chlorophenyl)ethyl]piperazine (d) 1-{4-[N-(2-ethoxyethyl)-N-chloroacetylamino]benzoyl}-4-[2-(4-chlorophenyl)ethyl]piperazine (e) 1-{4-[N-(2-phenoxyethyl)-N-chloroacetylamino]benzoyl}-4-[2-(4-chlorophenyl)ethyl]piperazine (f) 1-{4-[N-(3-methoxypropyl)-N-chloroacetylamino]benzoyl}-4-[2-(4-chlorophenyl)ethyl]piperazine.

EXAMPLE 71

Analogously to Example 7, 1-[2-(4-chlorophenyl)ethyl]piperazine and 4-chloroacetylaminocinnamic acid chloride are reacted to form 1-{3-[4-(N-chloroacetylamino)phenyl]prop-2-en-1-on-yl}-4-[2-(4-chlorophenyl)ethyl]piperazine.

EXAMPLE 72

Tablets, each comprising 50 mg of 1-{4-[N-(2-isopropyloxyethyl)-N-chloroacetylamino]benzoyl}-4-[2-(4-chlorophenyl)ethyl]piperazine or a salt, for example the hydrochloride, thereof, are prepared, for example, as follows:

| Composition (10000 tablets) | |
|---|---|
| active ingredient | 500.0 g |
| lactose | 500.0 g |
| potato starch | 352.0 g |
| gelatin | 8.0 g |
| talc | 60.0 g |
| magnesium stearate | 10.0 g |
| silica (highly dispersed) | 20.0 g |
| ethanol | q.s. |

The active ingredient is mixed with the lactose and 292 g of potato starch, and the mixture is moistened with an ethanolic solution of the gelatin and granulated through a sieve. After drying, the remaining potato starch, the magnesium stearate, the talc and the silica are mixed in and the mixture is compressed to form tablets which each weigh 145.0 mg and comprise 50.0 mg of active ingredient, and which may, if desired, be provided with dividing notches for finer adjustment of the dose.

EXAMPLE 73

Hard gelatin capsules, comprising 100 mg of active ingredient, e.g. 1-{4-[N-(2-isopropyloxyethyl)-N-chloroacetylamino]benzoyl}-4-[2-(4-chlorophenyl)ethyl]piperazine or a salt thereof, for example the hydrochloride, are prepared, for example, as follows:

| Composition (for 1000 capsules) | |
|---|---|
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added to the lyophilised active ingredient through a sieve having a mesh size of 0.2 mm. The two components are mixed intimately. Then, first the lactose is added through a sieve having a mesh size of 0.6 mm and then the microcrystalline cellulose through a sieve having a mesh size of 0.9 mm. Then the mixture is again mixed intimately for 10 minutes. Finally, the magnesium stearate is added through a sieve having a mesh size of 0.8 mm. After mixing for a further 3 minutes, size 0 hard gelatin capsules are each filled with 390 mg of the resulting formulation.

EXAMPLE 74

Film-coated tablets, each comprising 100 mg of 1-{4-[N-(2-isopropyloxyethyl)-N-chloroacetylamino]benzoyl}-4-[2-(4-chlorophenyl)ethyl]piperazine or a salt, for example the hydrochloride, thereof, are prepared, for example, as follows:

| Composition (for 1000 film-coated tablets) | |
|---|---|
| active ingredient | 100.0 g |
| lactose | 100.0 g |
| corn starch | 70.0 g |
| talc | 8.5 g |
| calcium stearate | 1.5 g |
| hydroxypropylmethylcellulose | 2.36 g |
| shellac | 0.64 g |
| water | q.s. |
| methylene chloride | q.s. |

The active ingredient, the lactose and 40 g of the corn starch are mixed, and the mixture is moistened with a paste, prepared from 15 g of the corn starch and water (with heating), and granulated. The granules are dried, and the remaining corn starch, the talc and the calcium stearate are added and mixed with the granules. The mixture is compressed to form tablets (weight: 280 mg), which are coated with a solution of the hydroxypropylmethylcellulose and the shellac in methylene chloride; final weight of the film-coated tablet: 283 mg.

EXAMPLE 75

A 0.2% injection or infusion solution of 1-{4-[N-(2-isopropyloxyethyl)-N-chloroacetylamino]benzoyl}-4-[2-(4-chlorophenyl)ethyl]piperazine, or of a salt, for example the hydrochloride, thereof, is prepared, for example, as follows:

| Composition (for 1000 ampoules) | |
|---|---|
| active ingredient | 5.0 g |
| sodium chloride | 22.5 g |
| phosphate buffer pH = 7.4 | 300.0 g |
| demineralised water | ad 2500.0 ml |

The active ingredient and the sodium chloride are dissolved in 1000 ml of water and filtered through a micro-filter. The buffer solution is added, and the mixture is made up to 2500 ml with water. To prepare unit dose forms, 1.0 or 2.5 ml are introduced into each glass ampoule, which then contains 2.0 or 5.0 mg, respectively, of active ingredient.

EXAMPLE 76

In a manner analogous to that described in Examples 72 to 75, it is also possible to prepare pharmaceutical compositions comprising a different compound mentioned in Examples 1 to 71.

What is claimed is:

1. A compound of formula I

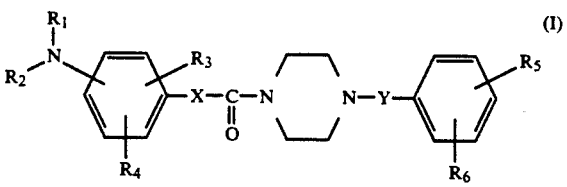

wherein
(a) $R_1$ is
 hydrogen,
 lower alkyl,
 lower alkoxy-lower alkyl,
 lower alkoxy-lower alkyl,
 phenyloxy-lower alkyl, wherein the phenyl group is unsubstituted or substituted by lower alkyl, trifluoromethyl, lower alkoxy, halogen and/or by hydroxy, phenyl-lower alkoxy-lower alkyl, wherein the phenyl group is unsubstituted or substituted by lower alkyl, trifluoromethyl, lower alkoxy, halogen and/or by hydroxy,
N-lower alkylamino-lower alkyl,
or N,N-di-lower alkylamino-lower alkyl and
$R_2$ is
lower alkenoyl,
(carboxy or lower alkoxycarbonyl)-lower alkenoyl,
halo-lower alkanoyl,
amino-lower alkanoyl,
N-lower alkylamino-lower alkanoyl,
N-lower alkanoyl,
N,N-di-lower alkylamino-lower alkanoyl,
pyrrolidino-lower alkanoyl,
piperidino-lower alkanoyl,
morpholino-lower alkanoyl,
thiomorpholino-lower alkanoyl,
piperazino-lower alkanoyl, wherein the piperazino radical is unsubstituted or substituted in the 4-position by lower alkyl or by lower alkanoyl,
hydroxy-lower alkanoyl,
lower alkoxy-lower alkanoyl,
lower alkanoyloxy-lower alkanoyl,
lower alkylthio-lower alkanoyl,
lower alkylsulfinyl-lower alkanoyl,
lower alkylsulfonyl-lower alkanoyl,
phenylthio-lower alkanoyl, wherein the phenyl group is unsubstituted or substituted by lower alkyl, trifluoromethyl, lower alkoxy, halogen and/or by hydroxy,
phenylsulfinyl-lower alkanoyl, wherein the phenyl group is unsubstituted or substituted by lower alkyl, trifluoromethyl, lower alkoxy, halogen and/or by hydroxy,
phenylsulfonyl-lower alkanoyl, wherein the phenyl group is unsubstituted or substituted by lower alkyl, trifluoromethyl, lower alkoxy, halogen and/or by hydroxy,
carboxy-lower alkanoyl,
lower alkoxycarbonyl-lower alkanoyl,
carbamoyl-lower alkanoyl,
N-lower alkylcarbamoyl-lower alkanoyl,
N,N-di-lower alkylcarbamoyl-lower alkanoyl,
cyano-lower alkanoyl,
carbamoyl,
N-lower alkylcarbamoyl,
N,N-di-lower alkylcarbamoyl,
carboxycarbonyl,
lower alkoxycarbonylcarbonyl,
(carbamoyl, N-lower alkylcarbamoyl,
or N,N-di-lower alkylcarbamoyl)-carbonyl; or
(b) $R_1$ is
lower alkoxy-lower alkyl,
lower alkoxy-lower alkoxy-lower alkyl,
phenyloxy-lower alkyl, wherein the phenyl group is unsubstituted or substituted by lower alkyl, trifluoromethyl, lower alkoxy, halogen and/or by hydroxy, or
phenyl-lower alkoxy-lower alkyl, wherein the phenyl group is unsubstituted or substituted by lower alkyl, trifluoromethyl, lower alkoxy, halogen and/or by hydroxy; and
$R_2$ is
hydrogen,
lower alkanoyl,
carboxy,
lower alkoxycarbonyl
or phenyl-lower alkoxycarbonyl, wherein the phenyl group is unsubstituted or substituted by lower alkyl, trifluoromethyl, lower alkoxy, halogen and/or by hydroxy;
$R_3$ and $R_4$ are each independently of the other
hydrogen,
lower alkyl,
halogen,
lower alkoxy
or lower alkylthio;
$R_5$ and $R_6$ are each independently of the other
hydrogen,
lower alkyl,
halo-lower alkyl,
lower alkoxy,
lower alkylthio,
halogen,
amino,
lower alkylamino,
di-lower alkylamino
or lower alkanoylamino; and
X and Y are each independently of the other
a direct bond,
lower alkylene
or lower alkenylene;
or a pharmaceutically acceptable salt thereof.

2. A compound of formula I according to claim 1 wherein $R_1$ is hydrogen, lower alkyl, lower alkoxy-lower alkyl, lower alkoxy-lower alkoxy-lower alkyl; phenyloxy-lower alkyl or phenyl-lower alkoxy-lower alkyl, the phenyl group in each of the two last-mentioned radicals being unsubstituted or substituted by lower alkyl, trifluoromethyl, lower alkoxy, halogen and/or by hydroxy; N-lower alkylamino-lower alkyl or N,N-di-lower alkylamino-lower alkyl, $R_2$ is lower alkenoyl, (carboxy or lower alkoxycarbonyl)-lower alkenoyl, halo-lower alkanoyl, amino-lower alkanoyl, N-lower alkylamino-lower alkanoyl, N-[(carboxy or lower alkoxycarbonyl)-lower alkylamino]-lower alkanoyl, N,N-di-lower alkylamino-lower alkanoyl, pyrralidino lower alkanoyl, piperidino-lower-alkanoyl, morpholino-lower alkanoyl, thiomorpholino-lower alkanoyl; piperazino-lower alkanoyl, the piperazino radical being unsubstituted or substituted in the 4-position by lower alkyl or by lower alkanoyl; hydroxy-lower alkanoyl, lower alkoxy-lower alkanoyl, lower alkanoyloxy-lower alkanoyl, lower alkylthio-lower alkanoyl, lower alkylsulfinyl-lower alkanoyl, lower alkylsulfonyl-lower alkanoyl; phenylthio-lower alkanoyl, phenylsulfinyl-lower alkanoyl or phenylsulfonyl-lower alkanoyl, the phenyl group in each of the three last-mentioned radicals being unsubstituted or substituted by lower alkyl, lower alkoxy, halogen and/or by hydroxy; carboxy-lower alkanoyl, lower alkoxycarbonyl-lower alkanoyl, carbamoyl-lower alkanoyl, N-lower alkylcarbamoyl-lower alkanoyl, N,N-di-lower alkylcarbamoyl-lower alkanoyl, cyano-lower alkanoyl, carbamoyl, N-lower alkylcarbamoyl, N,N-di-lower alkylcarbamoyl, carboxycarbonyl, lower alkoxycarbonylcarbonyl, (carbamoyl, N-lower alkylcarbamoyl or N,N-di-lower alkylcarbamoyl)-carbonyl, or, when $R_1$ is lower alkoxy-lower alkyl, lower alkoxy-lower alkoxy-lower alkyl, or phenyloxy-lower alkyl or phenyl-lower alkoxy-lower alkyl each unsubstituted or substituted as defined above, $R_2$ may also be hydrogen, lower alkanoyl, carboxy, lower alkoxycarbonyl or phenyl-lower alkoxycarbonyl, wherein the phenyl group is unsubstituted or substituted by lower alkyl, lower alkoxy, halogen and/or by hydroxy, $R_3$ and $R_4$ are each independently of the other hydrogen, lower alkyl, halogen, lower alkoxy or lower alkylthio, $R_5$ and $R_6$ are each independently of the other hydrogen, lower alkyl, halo-lower alkyl, lower alkoxy, lower alkylthio, halogen, amino, lower alkylamino, di-lower alkylamino or lower alkanoylamino, and X and Y are each independently of the other a direct bond, lower alkylene or lower alkenylene, or a salt thereof.

3. A compound of formula I according to claim 1 wherein $R_1$ is hydrogen, lower alkyl, lower alkoxy-lower alkyl, lower alkoxy-lower alkoxy-lower alkyl, phenyloxy-lower alkyl, N-lower alkylamino-lower alkyl or N,N-di-lower alkylamino-lower alkyl, $R_2$ is lower alkenoyl, (carboxy or lower alkoxycarbonyl)-lower alkenoyl, halo-lower alkanoyl, N-lower alkylamino-lower alkanoyl, N-[(carboxy or lower alkoxycarbonyl)-lower alkylamino]-lower alkanoyl, N,N-di-lower alkylamino-lower alkanoyl, piperidino-lower alkanoyl, hydroxy-lower alkanoyl, lower alkoxy-lower alkanoyl, lower alkanoyloxy-lower alkanoyl, lower alkylthio-lower alkanoyl, lower alkylsulfinyl-lower alkanoyl, lower alkylsulfonyl-lower alkanoyl, phenylthio-lower alkanoyl, phenylsulfinyl-lower alkanoyl, phenylsulfonyl-lower alkanoyl, carboxy-lower alkanoyl, lower alkoxycarbonyl-lower alkanoyl, N,N-di-lower alkylcarbamoyl or lower alkoxycarbonylcarbonyl, or, when $R_1$ is lower alkoxy-lower alkyl $R_2$ may also be hydrogen, lower alkanoyl, lower alkoxycarbonyl or phenyl-lower alkoxycarbonyl, $R_3$ and $R_4$ are each independently of the other hydrogen, lower alkyl, halogen, lower alkoxy or lower alkylthio, $R_5$ and $R_6$ are each independently of the other hydrogen, lower alkyl, trifluoromethyl, lower alkoxy, lower alkylthio, halogen or di-lower alkylamino, and X and Y are each independently of the other a direct bond, lower alkylene or lower alkenylene, or a salt thereof.

4. A compound of formula I according to claim 1 wherein $R_1$ is hydrogen, lower alkyl or lower alkoxy-lower alkyl, $R_2$ is lower alkenoyl or halo-lower alkanoyl, or, when $R_1$ is lower alkoxy-lower alkyl, $R_2$ may also be hydrogen, $R_3$ and $R_4$ are each hydrogen, $R_5$ is chlorine, $R_6$ is hydrogen, X is a direct bond and Y is 1,2-ethylene, or a pharmaceutically acceptable salt thereof.

5. A compound according to claim 1 of formula Ia

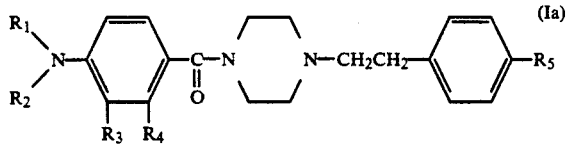

wherein (a) $R_1$ is hydrogen, lower alkyl or lower alkoxy-lower alkyl, and $R_2$ is lower alkenoyl, lower alkanoyl substituted by halogen, di-lower alkylamino, pyrrolidino, piperidino, lower alkylthio, lower alkylsulfinyl or lower alkylsulfonyl, or (b) $R_1$ is lower alkoxy-lower alkyl and $R_2$ is hydrogen, $R_3$ and $R_4$ are each independently of the other hydrogen, lower alkyl, chlorine, fluorine or bromine, and $R_5$ is lower alkylthio, chlorine, fluorine or bromine, or a pharmaceutically acceptable salt thereof.

6. A compound of formula Ia according to claim 5 wherein $R_1$ is hydrogen, lower alkyl or lower alkoxy-lower alkyl, $R_2$ is lower alkanoyl substituted by halogen, lower alkylthio, lower alkylsulfinyl or by lower alkylsulfonyl, or, when $R_1$ is lower alkoxy-lower alkyl, $R_2$ may also be hydrogen, $R_3$ and $R_4$ are each independently of the other hydrogen, lower alkyl, chlorine, fluorine or bromine, and $R_5$ is lower alkylthio, chlorine, fluorine or bromine, or a salt thereof.

7. A compound of formula Ia according to claim 5 wherein $R_1$ is hydrogen, $C_1$-$C_4$alkyl or $C_1$-$C_4$alkoxy-$C_2$-$C_4$alkyl, $R_2$ is $C_3$-$C_7$alkenoyl, chloro-$C_2$-$C_4$alkanoyl, $C_1$-$C_4$alkylthio-, $C_1$-$C_4$alkylsulfinyl- or $C_1$-$C_4$alkylsulfonyl-$C_2$-$C_4$alkanoyl, or, when $R_1$ is $C_1$-$C_4$alkoxy-$C_2$-$C_4$alkyl, $R_2$ may also be hydrogen, $R_3$ and $R_4$ are each independently of the other hydrogen, $C_1$-$C_4$alkyl, fluorine or chlorine, and $R_5$ is chlorine, or a pharmaceutically acceptable salt thereof.

8. A compound of formula I according to claim 1 wherein $R_1$ is hydrogen, methyl, ethyl or 2-isopropyloxyethyl, $R_2$ is prop-2-enoyl, chloroacetyl, 3-chloropropionyl, methylthioacetyl or ethylthioacetyl, $R_3$ and $R_4$ are each hydrogen, methyl, fluorine or chlorine, and $R_5$ is chlorine, or a pharmaceutically acceptable salt thereof.

9. 1-{4-[N-(2-Isopropyloxyethyl)amino]benzoyl}-4-[2-(4-chlorophenyl)ethyl]piperazine according to claim 1, or a pharmaceutically acceptable salt thereof.

10. 1-{4-[N-(2-Isopropyloxyethyl)-N-chloroacetylamino]benzoyl}-4-[2-(4-chlorophenyl)ethyl]piperazine according to claim 1, or a pharmaceutically acceptable salt thereof.

11. 1-[4-(Acryloylamino)benzoyl]-4-[2-(4-chlorophenyl)ethyl]piperazine according to claim 1, or a pharmaceutically acceptable salt thereof.

12. 1-{4-[N-(2-Isopropyloxyethyl)-N-chloroacetylamino]benzoyl}-4-[2-2-(4-bromophenyl)ethyl]piperazine according to claim 1, or a pharmaceutically acceptable salt thereof.

13. A pharmaceutical composition comprising a therapeutically effective amount of a compound according to claim 1 and a pharmaceutically acceptable carrier.

14. A pharmaceutical composition according to claim 13 comprising 1-{4-[N-(2-isopropyloxyethyl)-N-chloroacetylamino]benzoyl}-4-[2-(4-chlorophenyl)ethyl]piperazine or a pharmaceutically acceptable salt thereof.

15. A method for the treatment of disorders that are responsive to the inhibition of interleukin-1 comprising administering to a warm blooded organism a therapeutically effective amount of a compound of formula I according to claim 1 or a pharmaceutically acceptable salt thereof.

16. A method for the treatment of disorders that are responsive to the inhibition of interleukin-1 comprising administering to a warm blooded organism a therapeutically effective amount of a compound according to claim 10 or a pharmaceutically acceptable salt thereof.

* * * * *

UNITED STATES PATENT AND TRADEMARK OFFICE
CERTIFICATE OF CORRECTION

PATENT NO. : 5,286,728
DATED : Feb. 15, 1994
INVENTOR(S) : Pier G. Ferrini

It is certified that error appears in the above-identified patent and that said Letters Patent is hereby corrected as shown below:

Column 33, line 14, delete "N-lower alkanoyl" and insert

-- N-[(carboxy or lower alkoxycarbonyl)-lower alkylamino]-lower alkanoyl -- in lieu thereof.

Column 36, please delete line 40 and insert

-- chloroacetylamino]benzoyl}-4-[2-(4-bromophenyl)e- --

Signed and Sealed this

Twelfth Day of July, 1994

Attest:

BRUCE LEHMAN

*Attesting Officer*    *Commissioner of Patents and Trademarks*